(12) United States Patent
O'Shannessy et al.

(10) Patent No.: US 9,915,660 B2
(45) Date of Patent: Mar. 13, 2018

(54) METHODS FOR DETERMINING PROGNOSIS OF COLORECTAL CANCER

(71) Applicant: MORPHOTEK, INC., Exton, PA (US)

(72) Inventors: Daniel John O'Shannessy, Schwenksville, PA (US); Nicholas C. Nicolaides, Glen Mills, PA (US); Elizabeth B. Somers, West Grove, PA (US)

(73) Assignee: Morphotek, Inc., Exton, PA (US)

( * ) Notice: Subject to any disclaimer, the term of this patent is extended or adjusted under 35 U.S.C. 154(b) by 0 days.

(21) Appl. No.: 14/770,840

(22) PCT Filed: Mar. 15, 2014

(86) PCT No.: PCT/US2014/029898
§ 371 (c)(1),
(2) Date: Aug. 27, 2015

(87) PCT Pub. No.: WO2014/145181
PCT Pub. Date: Sep. 18, 2014

(65) Prior Publication Data
US 2016/0003829 A1    Jan. 7, 2016

Related U.S. Application Data

(60) Provisional application No. 61/793,565, filed on Mar. 15, 2013.

(51) Int. Cl.
*G01N 33/574* (2006.01)

(52) U.S. Cl.
CPC .......... *G01N 33/57419* (2013.01); *G01N 2333/4742* (2013.01); *G01N 2333/71* (2013.01); *G01N 2333/78* (2013.01)

(58) Field of Classification Search
None
See application file for complete search history.

(56) References Cited

U.S. PATENT DOCUMENTS

| | | | |
|---|---|---|---|
| 7,219,016 B2 | 5/2007 | Rimm et al. | |
| 2009/0034823 A1 | 2/2009 | Christiansen et al. | |
| 2009/0305277 A1 | 12/2009 | Baker et al. | |
| 2011/0311123 A1 | 12/2011 | Gholap et al. | |
| 2012/0093387 A1 | 4/2012 | Gholap et al. | |

FOREIGN PATENT DOCUMENTS

| | | |
|---|---|---|
| WO | WO-2007-016367 A2 | 2/2007 |
| WO | WO-2007-021860 A2 | 2/2007 |
| WO | WO 2012/052757 A1 | 4/2012 |
| WO | WO 2012/166824 A2 | 12/2012 |
| WO | WO-2013-024015 A1 | 2/2013 |

OTHER PUBLICATIONS

Haab (2006) "Applications of antibody array platforms", Current Opinion in Biotechnology, 17: 415-21:1-7.*
Voduc, et al. (2008) "Tissue Microarrays in Clinical Oncology", Seminars in Radiation Oncology, 18(2): 89-97.*
Kummar, et al. (2002) British Journal of Cancer, 86(12): 1884-87.*
Arentz, et al. (2011) "Desmin expression in colorectal cancer stroma correlates with advanced stage disease and marks angiogenic microvessels", Clinical Proteomics, 8:16, pp. 1-13.*
Hasebe, et al. (2003) "Proliferative activities of tumor stromal cells play important roles in tumor thickness and progression of T3 ulcerative-type colorectal cancer", Virchows Archiv, 442(6): 569-76.*
Rmali, et al (2005) "Prognostic values of tumor endothelial markers in patients with colorectal cancer" World Journal of Gastroenterology, 11(9): 1283-86.*
Kwong, et al. (2005) "Synchronous global assessment of gene and protein expression in colorectal cancer progression", Genomics, 86(2): 142-58.*
Wehler (2008) "PDGFRalpha/beta expression correlates with the metastatic behavior of human colorectal cancer: a possible rationale for a molecular targeting strategy", Oncology Report, 19(3): 697-704.*
Coulson-Thomas, et al. (2011) "Colorectal cancer desmoplastic reaction up-regulates collagen synthesis and restricts cancer cell invasion", Cell Tissue Research, 346: 223-36.*
Imamura, et al. (2009) "HIF-1α and HIF-2α have divergent roles in colon cancer", International Journal of Cancer, 124(4): 763-71.*
Xing, et al. (2011) "The antitumor activity of exogenous and endogenous canstatin on colorectal cancer cells", Asian Pacific Journal of Cancer Prevention, 12(10): 2713-16.*
Meeh, et al. (2009) "A Gene Expression Classifier of Node-Positive Colorectal Cancer", Neoplasia, 11(10): 1074-83.*
Christian, et al. (2008) "Endosialin (Tem1) Is a Marker of Tumor-Associated Myofibroblasts and Tumor Vessel-Associated Mural Cells", American Journal of Paathology, 172(2): 486-94.*
Gonzalez-Pons, et al. (2015) "Colorectal Cancer Biomarkers: Where Are We Now?", Biomedical Research International, Article ID 147014, 14 pages long.*

(Continued)

*Primary Examiner* — Robert M Kelly
(74) *Attorney, Agent, or Firm* — Baker & Hostetler LLP

(57) ABSTRACT

Provided herein are methods for determining the risk that a subject diagnosed with colorectal cancer will develop a recurrence of colorectal cancer and methods of predicting clinical outcome for a subject diagnosed with colorectal cancer by a) determining the level of expression for each marker of a panel of markers in a panel of tumor compartments in a tumor tissue sample from the subject, wherein the panel of markers comprises at least two of TEM1, HIF2α, CAIX, PDGFRβ, fibronectin, collagen I, collagen IV, and CD31 and wherein the panel of tumor compartments comprises at least three tumor compartments of pure stroma, tumor, stromal vessel, and tumor vessel; b) determining the TAPPS score for said subject; and c) comparing the TAPPS score of the subject to the TAPPS score of a population of subjects diagnosed with colorectal cancer. Also provided are related computer-implemented methods and systems, kits, and tumor microarrays.

14 Claims, 13 Drawing Sheets

(56) References Cited

OTHER PUBLICATIONS

Hod, "A Simplified Ribonuclease Protection Assay", Biotechniques, 1992, 13(6), 852-854.

Parker & Barnes, "mRNA: Detection by in Situ and Northern Hybridization", Methods in Molecular Biology, 1999, 106, 247-283.

Saeed, et al., "TM4" A Free, Open-Source System for Microarray Data Management and Analysis, Biotechniques, Feb. 2003, 34(2), 374-8.

Weis, et al., "Detection of Rare mRNAs via Quantitative RT-PCR", Trends in Genetics, Aug. 1992, 8(8), 263-264.

Dubucquoy et al., "Molecular and clinico-pathological markers in rectal cancer: a tissue micro-array study", International Journal of Colorectal Disease, Gastroenterology and Surgery, Springer, Berlin, DE, 2008, 24(2):129-138.

Midulla et al., "Source of Oncofetal ED-B-containing Fibronectin: Implications of Production of Both Tumor and Endothelial Cells[1]", Cancer Research, 2000, 60, 164-169.

O'Shannessy et al., "Influence of tumor microenvironment on prognosis in colorectal cancer: tissue architecture-dependent signature of endosialin (TEM-1) and associated proteins", Oncotarget, 2014, 5(12):3983-3995.

Rmali et al., "Prognostic values of tumor endothelial markers in patients with colorectal cancer", World Journal of Gastroenterology, 2005, 11(9):1283-1386.

\* cited by examiner

METHODS FOR DETERMINING PROGNOSIS OF COLORECTAL CANCER

CROSS-REFERENCE TO RELATED APPLICATIONS

This application is the National Stage of International Application No. PCT/US2014/029898, filed Mar. 15, 2014, which claims the benefit of U.S. provisional application No. 61/793,565, filed Mar. 15, 2013, the disclosures of which are incorporated herein by reference in their entireties.

TECHNICAL FIELD

The present invention provides a set of biomarkers, the expression levels of which are useful for determining the risk that a subject diagnosed with colorectal cancer will develop a recurrence of colorectal cancer and for predicting clinical outcome for a subject diagnosed with colorectal cancer.

BACKGROUND

In 2013, about 143,000 people in the United States will be diagnosed with colorectal cancer. In that same year, an estimated 50,830 deaths from colorectal cancer will occur in the United States. Colorectal cancer is the fourth most common cancer in men, after skin, prostate, and lung cancer. It is also the fourth most common cancer in women, after skin, breast, and lung cancer. Methods for determining risk of recurrence or prognosis in colorectal cancer patients would be of great benefit for guiding treatment decisions for these patients. Described herein is the generation of an independently significant, multi-marker prognostic method for colorectal cancer. The data demonstrate the potential for multi-marker assays in improving prognostic assessment of colorectal cancer. The methods described herein allow assignment of a subject at the time of diagnosis of colorectal cancer into a high risk for recurrence or a low risk for recurrence group. The methods will assist patients and physicians in determining the need for adjuvant intervention or at least aggressive follow-up surveillance. The goal of the described methods is to improve the overall survival of the high risk patient group without exposing the remaining patients to the risks and costs associated with adjuvant therapy or monitoring for recurrence of disease.

SUMMARY

Described herein are methods for determining the risk that a subject diagnosed with colorectal cancer will develop a recurrence of this disease based on gene expression profiling of a panel of biomarkers in particular histological compartments of a tumor tissue sample obtained from the subject. Also described are methods of predicting clinical outcome for a subject diagnosed with colorectal cancer based on gene expression profiling of a panel of biomarkers in particular tumor compartments of a tumor tissue sample obtained from the subject. Further provided herein are methods of differential diagnosis that allow assignment of a subject diagnosed with colorectal cancer to be assigned to a high risk or low risk category for TEM-1-expressing colorectal cancer. Also described are materials and methods for producing tissue sample arrays labeled with detection agents that allow for analysis of the tissue sample in order to predict various risks associated with the occurrence of colorectal cancer. The described tissue sample arrays may also be used to analyze tissue samples in order to assist in determining a beneficial course of treatment for an individual diagnosed with colorectal cancer. Kits having reagents suitable to label tissue samples or tissue arrays discussed herein are also described herein.

BRIEF DESCRIPTION OF THE DRAWINGS

FIG. 4(A-G) provides a graphical representation of marker expression by histological compartment (tumor, stromal vessel, tumor vessel, or stroma).

DETAILED DESCRIPTION OF ILLUSTRATIVE EMBODIMENTS

Figure 1:
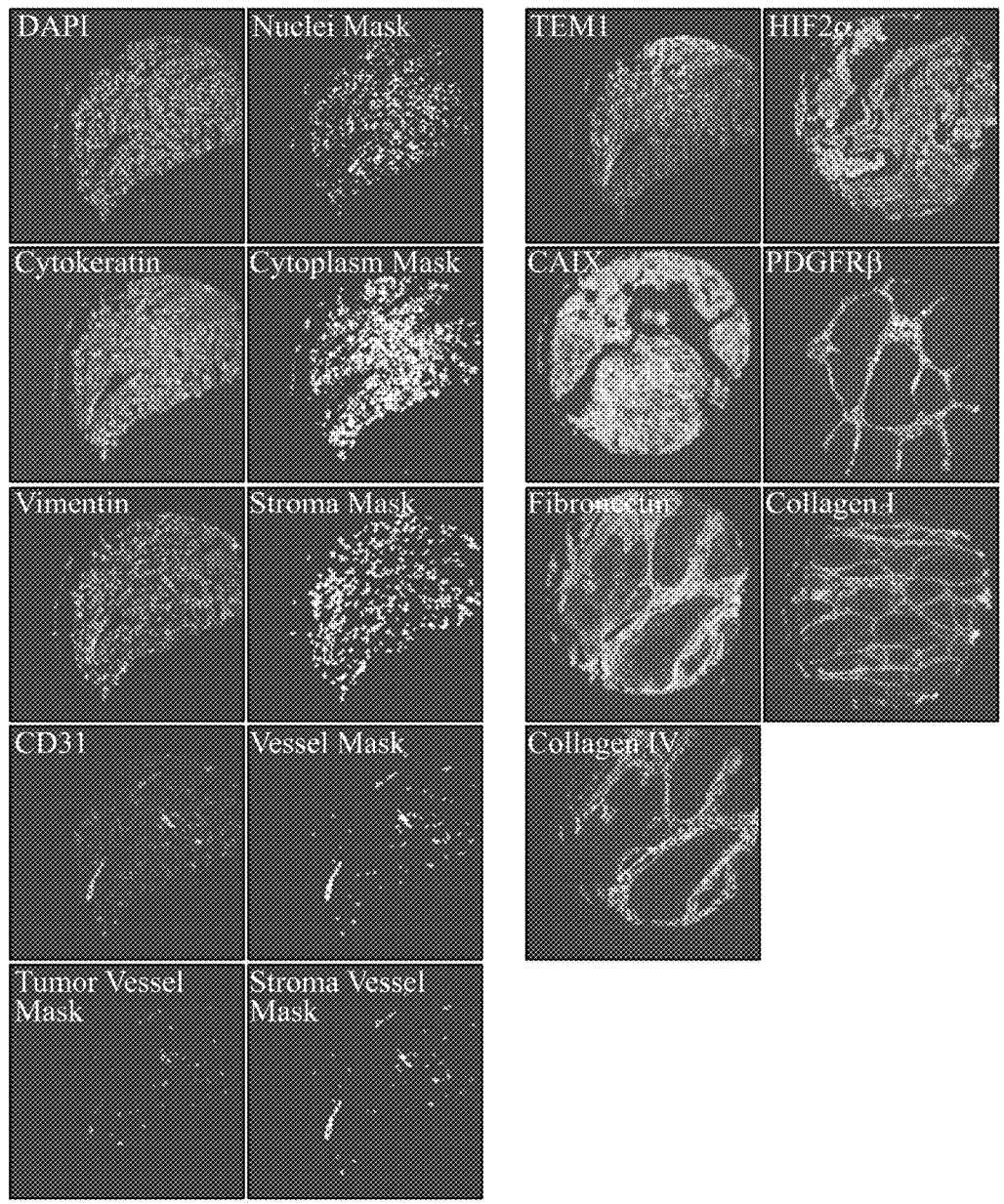
FIG. 1 illustrates biological compartment masking and a representative biomarker panel. (A) Representative image examples from each fluorescence channel used to generate biological compartment masks during AQUA® analysis. DAPI was used to generate a nuclei mask, fluorescein isothiocyanate (FITC) was used to label cytokeratin to identify tumor cytoplasm, Cy3 was used to label vimentin to identify stroma, Cy7 was used to label CD31 to identify vasculature and in conjunction with cytokeratin to determine tumor vasculature and with vimentin to identify stromal vasculature. (B) Representative image examples of the seven biomarker panel (Cy5).

Unless defined otherwise, technical and scientific terms used herein have the same meaning as commonly understood by one of ordinary skill in the art to which this invention belongs. Singleton et al., Dictionary of Microbiology and Molecular Biology 3rd ed., J. Wiley & Sons (New York, N.Y. 2006), and March, Advanced Organic Chemistry Reactions, Mechanisms and Structure 6th ed., John Wiley & Sons (New York, N.Y. 2007), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in this specification and the appended claims, the singular forms "a," "an," and "the" include plural referents unless the content clearly dictates otherwise. Thus, for example, reference to "a cell" includes a combination of two or more cells, and the like.

The term "about" (also denoted by the symbol "~") as used herein when referring to a measurable value such as an amount, a temporal duration, and the like, is meant to encompass variations of up to ±10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications.

As used herein, the term "antibody" refers to all isotypes of immunoglobulins (IgG, IgA, IgE, IgM, IgD, and IgY) including various monomeric and polymeric forms of each isotype, and should be understood to encompass antigen-binding fragments, diabodies and single-chain molecules as well as Fab, F(ab')2, Fc, Fabc, and Fv molecules, single chain (Sc) antibodies, individual antibody light chains, individual antibody heavy chains, chimeric fusions between antibody chains or CDRs and other proteins, protein scaffolds, heavy chain monomers or dimers, light chain monomers or dimers, dimers consisting of one heavy and one light chain, and the like.

Antigen-binding fragments are any proteinaceous structure that may exhibit binding affinity for a particular antigen. Some antigen-binding fragments are composed of portions of intact antibodies that retain antigen-binding specificity of the parent antibody molecule. For example, antigen-binding fragments may comprise at least one variable region (either a heavy chain or light chain variable region) or one or more CDRs of an antibody known to bind a particular antigen. Examples of suitable antigen-binding fragments include, without limitation diabodies and single-chain molecules as well as Fab, F(ab')2, Fc, Fabc, and Fv molecules, single chain (Sc) antibodies, individual antibody light chains, individual antibody heavy chains, chimeric fusions between antibody chains or CDRs and other proteins, protein scaffolds, heavy chain monomers or dimers, light chain monomers or dimers, dimers consisting of one heavy and one light chain, and the like. All antibody isotypes may be used to produce antigen-binding fragments. Additionally, antigen-binding fragments may include non-antibody proteinaceous frameworks that may successfully incorporate polypeptide segments in an orientation that confers affinity for a given antigen of interest, such as protein scaffolds. Antigen-binding fragments may be recombinantly produced or produced by enzymatic or chemical cleavage of intact antibodies. The phrase "an antibody or antigen-binding fragment thereof" may be used to denote that a given antigen-binding fragment incorporates one or more amino acid segments of the antibody referred to in the phrase.

"Specific binding" when used in the context of antibodies, or antibody fragments, represents binding via domains encoded by immunoglobulin genes or fragments of immunoglobulin genes to one or more epitopes of a protein of interest, without preferentially binding other molecules in a sample containing a mixed population of molecules. Typically, an antibody binds to a cognate antigen with a $K_d$ of less than about $1 \times 10^{-8}$ M, as measured by a surface plasmon resonance assay or a cell binding assay. Phrases such as "[antigen]-specific" antibody (e.g., TEM-1-specific antibody) are meant to convey that the recited antibody specifically binds the recited antigen.

The term "tumor," as used herein, refers to all neoplastic cell growth and proliferation, and all pre-cancerous and cancerous cells and tissues.

The terms "cancer" and "cancerous" refer to or describe the physiological condition in mammals that is typically characterized by unregulated cell growth. An example of cancer is colorectal cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

The term "colorectal cancer" is used in the broadest sense and refers to (1) all stages and all forms of cancer arising from epithelial cells of the large intestine and/or rectum and/or (2) all stages and all forms of cancer affecting the lining of the large intestine and/or rectum. In the staging systems used for classification of colorectal cancer, the colon and rectum are treated as one organ.

According to the tumor, node, metastasis (TNM) staging system of the American Joint Committee on Cancer (AJCC) (Edge et al. (eds.), AJCC Cancer Staging Manual. 7th Ed. New York, N.Y.: Springer; 2009), the various stages of colorectal cancer are defined as follows:

Tumor T0: no evidence of primary tumor; T1: tumor invades submucosa; T2: tumor invades muscularis propria; T3: tumor invades through the muscularis propria into the subserose, or into the pericolic or perirectal tissues; T4: tumor directly invades other organs or structures, and/or perforates;

Node: N0: no regional lymph node metastasis; N1: metastasis in 1 to 3 regional lymph nodes; N2: metastasis in 4 or more regional lymph nodes;

Metastasis: M0: no distant metastasis; M1: distant metastasis present; Stage groupings: Stage I: T1 N0 M0; T2 N0 M0; Stage II: T3 N0 M0; T4 N0 M0; Stage III: any T, N1-2; M0; Stage IV: any T, any N, M1.

According to the Modified Duke Staging System, the various stages of colorectal cancer are defined as follows:

Stage A: the tumor penetrates into the mucosa of the bowel wall but not further;

Stage B: tumor penetrates into and through the muscularis propria of the bowel wall;

Stage C: tumor penetrates into but not through muscularis propria of the bowel wall, there is pathologic evidence of colorectal cancer in the lymph nodes; or tumor penetrates into and through the muscularis propria of the bowel wall, there is pathologic evidence of cancer in the lymph nodes;

Stage D: tumor has spread beyond the confines of the lymph nodes, into other organs, such as the liver, lung or bone.

Prognostic factors are those variables related to the natural history of colorectal cancer, which influence the recurrence rates and outcome of patients once they have developed colorectal cancer. Clinical parameters that have been associated with a worse prognosis include, for example, lymph node involvement and high grade tumors. Prognostic factors are frequently used to categorize patients into subgroups with different baseline relapse risks.

The term "prognosis" is used herein to refer to the prediction of the likelihood of cancer-attributable death or progression, including recurrence, metastatic spread, and drug resistance, of a neoplastic disease, such as colorectal cancer.

The term "prediction" is used herein to refer to the likelihood that a patient will have a particular clinical outcome, whether positive or negative. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as surgical intervention. The prediction may include prognostic factors.

The term "positive clinical outcome" means an improvement in any measure of patient status, including those measures ordinarily used in the art, such as an increase in the duration of Recurrence-Free interval (RFI), an increase in the time of Overall Survival (OS), an increase in the time of Disease-Free Survival (DFS), an increase in the duration of Distant Recurrence-Free Interval (DRFI), and the like.

The term "risk classification" means the level of risk or the prediction that a subject will experience a particular clinical outcome. A subject may be classified into a risk group or classified at a level of risk based on the predictive methods of the present invention. A "risk group" is a group of subjects or individuals with a similar level of risk for a particular clinical outcome.

The term "subject" or "patient" refers to human and non-human animals, including all vertebrates, e.g., mammals and non-mammals, such as non-human primates, mice, rabbits, sheep, dogs, cats, horses, cows, chickens, amphibians, and reptiles. In many embodiments of the described methods, the subject is a human.

The terms "treating" or "treatment" refer to any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. Treatment may be assessed by objective or subjective parameters; including the results of a physical examination, neurological examination, or psychiatric evaluations.

The term "long-term" survival is used herein to refer to survival for at least 3 years, more preferably for at least 5 years.

The term "Recurrence-Free Interval (RFI)" is used herein to refer to time to first colorectal cancer recurrence censoring for second primary cancer as a first event or death without evidence of recurrence.

The term "Progression-Free Survival (PFS)" is used herein to refer to time from first-line treatment of colorectal cancer until disease progression or death, during which time the disease is present but does not get worse.

The term "Overall Survival (OS)" is used herein to refer to time from surgery to death from any cause.

The term "Disease-Free Survival (DFS)" is used herein to refer to time to colorectal cancer recurrence or death from any cause.

The term "Distant Recurrence-Free Interval (DRFI)" is used herein to refer to the time from surgery to the first anatomically distant cancer recurrence.

In the context of the present invention, reference to "at least one," "at least two," "at least five," etc. of the genes listed in any particular gene set means any one or any and all combinations of the genes listed.

The term "node negative" cancer, such as "node negative" colorectal cancer, is used herein to refer to cancer that has not been detected in and/or has not spread to the lymph nodes. The term "node positive" cancer, such as "node positive" colorectal cancer, is used herein to refer to cancer that has spread to and/or been detected in the lymph nodes.

Methods

Described herein are methods for determining the risk that a subject diagnosed with colorectal cancer will develop a recurrence of this disease based on gene expression profiling of a panel of biomarkers in particular tumor compartments of a tumor tissue sample obtained from the patient. Also described are methods of predicting clinical outcome for a subject diagnosed with colorectal cancer based on gene expression profiling of a panel of biomarkers in particular tumor compartments of a tumor tissue sample obtained from the patient. Further provided herein are methods of differential diagnosis that allow assignment of a subject diagnosed with colorectal cancer to be assigned to a high risk or low risk category for TEM-1-expressing colorectal cancer.

The subject may be lymph node-positive or lymph node-negative for colorectal cancer. The patient's colorectal cancer may be at any stage, though most often will be Stage I, Stage II, or Stage III cancer.

The tumor tissue sample may be fixed, fixed and paraffin-embedded, or fresh. In some aspects, the tumor tissue sample is obtained from a tissue biopsy, a fine needle aspiration sample, surgically resected tumor tissue, or histological preparations of a biological sample obtained from the patient. In some embodiments, the tumor tissue sample is from the primary colorectal cancer tumor. In other embodiments, the tumor tissue sample of from a metastatic colorectal cancer tumor.

The panel of markers includes at least two of tumor endothelial marker-1 (TEM1; also known as endosialin or CD248), hypoxia inducible factor 2 alpha (HIF2α), carbonic anhydrase 9 (CAIX), platelet-derived growth factor receptor beta (PDGFRβ), fibronectin (FN), collagen I (COLI), collagen IV (COLIV), and CD31. In preferred embodiments, the panel of markers includes three, four, five, six, seven, or all eight of TEM1, HIF2α, CAIX, PDGFRβ, fibronectin, collagen I, collagen IV, and CD31. In some embodiments, the panel of markers includes at least TEM1 and CAIX. In some aspects, the panel of markers includes at least TEM1, HIF2α, CAIX, and PDGFRβ; more preferably, TEM1, HIF2α, CAIX, fibronectin, and PDGFRβ; and in some embodiments, TEM1, HIF2α, CAIX, PDGFRβ, fibronectin, collagen I, collagen IV, and CD31.

The markers are localized to a panel of tumor compartments including at least three of pure stroma (stroma that is substantially or completely free of vasculature), tumor, stromal vessel, and tumor vessel. The localization may involve identifying and/or labeling the at least three compartments in the tumor tissue sample from the subject. In preferred embodiments, the panel of tumor compartments to which the biomarkers are localized includes pure stroma, tumor, stromal vessel, and tumor vessel.

In some aspects, the methods described herein involve determining the expression level of at least two, three, four, or five of the following biomarker and tumor compartment combinations: the expression level of TEM1 in tumor stroma, the expression level of TEM1 in tumor vessel, the expression level of HIF2α in stroma vessel, the expression level of HIF2α in tumor stroma, the expression level of CAIX in tumor vessel, the expression level of PDGFRβ in tumor stroma, and the expression level of fibronectin (e.g., fibronectin-1) in tumor stroma. In preferred embodiments of the methods described, the expression level of TEM1 in tumor stroma, the expression level of TEM1 in tumor vessel, the expression level of HIF2α in stroma vessel, the expression level of HIF2α in tumor stroma, the expression level of CAIX in tumor vessel, and the expression level of PDGFRβ in tumor stroma are determined. In some preferred embodiments of the described methods, the expression level of TEM1 in tumor stroma, the expression level of TEM1 in tumor vessel, the expression level of HIF2α in stroma vessel, the expression level of HIF2α in tumor stroma, the expression level of CAIX in tumor vessel, the expression level of PDGFRβ in tumor stroma, and the expression level of fibronectin in tumor stroma are determined. In some embodiments of the described methods, the expression level of TEM1 in stroma, the expression level of TEM1 in tumor vessel, the expression level of HIF2α in stroma vessel, the expression level of COLIV in tumor, and the expression level of fibronectin in stroma are determined. In some embodiments of the described methods, the expression level of TEM1 in stroma, the expression level of COLIV in tumor, and the expression level of fibronectin in stroma are determined. In the methods described herein, at least one subcellular compartment (e.g., cell nucleus, a cytoplasm, a nuclear membrane, a cellular membrane, a mitochondria, an endoplasmic reticulum, a peroxisome, and a lysosome) may also be identified or labeled.

Expression levels of the biomarkers may be determined by any method known in the art. Methods of gene expression profiling include methods based on hybridization analysis of polynucleotides, methods based on sequencing of polynucleotides, and proteomics-based methods. The most commonly used methods known in the art for the quantification of mRNA expression in a sample include northern blotting and in situ hybridization (Parker & Barnes, Methods in Molecular Biology 106:247-283 (1999)); RNAse protection assays (Hod, Biotechniques 13:852-854 (1992)); and PCR-based methods, such as reverse transcription polymerase chain reaction (RT-PCR) (Weis et al., Trends in Genetics 8:263-264 (1992)). Alternatively, antibodies may be employed that can recognize sequence-specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). Expression levels of the biomarkers may also be determined by immunohistochemical methods and automated tissue microarray analyses (e.g., see U.S. Pub. Nos. 20120093387 and 20110311123, incorporated by reference herein.)

The methods provided herein may be automated in whole or in part. In some embodiments, the methods involve the quantitative immunofluorescence (QIF) signal of the panel of markers in a sample of the patient's colorectal cancer tumor. Numerous quantitative image analysis procedures are known in the art. An example of a quantitative image analysis procedure that may be used to determine the level of expression is automated quantitative analysis (AQUA®) technology, as described in issued U.S. Pat. No. 7,219,016, and in U.S. Patent Application Publication No. 2009/0034823, each of which is incorporated by reference into this application in its entirety. The AQUA® technology permits quantification not only of the fluorescence signal for a given marker within the tissue sample under analysis, but also permits compartmentalization within molecularly defined tumor and subcellular compartments.

The subject's levels of expression of the biomarkers within the panel of tumor compartments allows the determination of a TEM1-Associated Pathway Prognostic Signature (TAPPS) score for the patient (as used herein, the term "TAPPS" may also be used in place of the term "R-TAPPS" which is a refined version of the originally defined TAPPS score, as explained in the examples section, below). The subject's TAPPS score is generated by incorporating the subject's expression levels of the biomarkers within the panel of tumor compartments in a TAPPS equation. The TAPPS equation is generated by examining the expression profiles of the biomarker panel in the panel of tumor compartments of a population of subjects diagnosed with colorectal cancer in a multivariate Cox Proportional Hazards model using backwards elimination employing univariate cut-points to provide the prognostic model that meets the desired p-value level. From this model, a coefficient is derived for each marker, and, with these coefficients, a TAPPS equation is developed that provides an overall risk score. In some embodiments, the TAPPS equation is determined by determining the coefficients A, B, C, D, etc. for each of the markers in each of the tumor compartments selected for inclusion for the population of colorectal cancer patients to provide a prognostic model having an acceptable p value. In some embodiments, the TAPPS equation is $$(\sim A*TEM1\_Stroma)+$$
$$(\sim B*TEM1\_TumorVasculature)+$$
$$(\sim C*CAIX\_TumorVasculature)+$$
$$(\sim D*CAIX\_Tumor).$$

wherein coefficients A, B, C, and D are the coefficients derived for each respective marker in each respective tumor compartment in the multivariate Cox Proportional Hazards model using backwards elimination employing univariate cut-points to provide the prognostic model for the given population of colorectal cancer patients. In other embodiments, the TAPPS equation is:

(~$A$*TEM1_Stroma)+
   (~$B$*TEM1_TumorVasculature)+
   (~$C$*HIF2α_StromaVasculature)+
   (~$D$*HIF2α_Stroma)+
   (~$E$*CAIX_TumorVasculature)+
   (~$F$*CAIX_Tumor)+(~$G$*PDGFRβ_Stroma)+
   (~$H$*Fibronectin_Stroma)

wherein coefficients A, B, C, D, E, F, G, and H are the coefficients derived for each respective marker in each respective tumor compartment in the multivariate Cox Proportional Hazards model using backwards elimination employing univariate cut-points to provide the optimal prognostic model for the given population of colorectal cancer patients. In some embodiments, the TAPPS equation is as follows:

(~−1.063*TEM1_Stroma)+
   (~0.478*TEM1_TumorVasculature)+(~−
   1.095*HIF2α_StromaVasculature)+
   (~0.407*HIF2α_Stroma)+(~−
   1.096*CAIX_TumorVasculature)+
   (~0.912*CAIX_Tumor)+
   (~0.600*PDGFRβ_Stroma)+
   (~0.714*Fibronectin_Stroma).

In some embodiments, the TAPPS equation is (~$A$*TEM1_Stroma)+
   (~$B$*TEM1_TumorVasculature)+
   (~$C$*HIF2α_StromaVasculature)+
   (~$D$*COLIV_Tumor)+(~$E$*$FN$ stroma).

wherein coefficients A, B, C, D, and E are the coefficients derived for each respective marker in each respective tumor compartment in the multivariate Cox Proportional Hazards model using backwards elimination employing univariate cut-points to provide the prognostic model for the given population of colorectal cancer patients. In some embodiments, the TAPPS equation is (~−0.89*TEM1_Stroma)+
   (~1.19*TEM1_TumorVasculature)+(~−
   0.76*HIF2α_StromaVasculature)+(~0.62*CO-
   LIV_Tumor)+(~0.83*$FN$ stroma).

wherein coefficients A, B, C, D, and E are the coefficients derived for each respective marker in each respective tumor compartment in the multivariate Cox Proportional Hazards model using backwards elimination employing univariate cut-points to provide the prognostic model for the given population of colorectal cancer patients. In some embodiments, the TAPPS equation is (~$A$*TEM1_Stroma)+($B$*COLIV_Tumor)+(~$C$*$FN$ stroma).

wherein coefficients A, B, and C are the coefficients derived for each respective marker in each respective tumor compartment in the multivariate Cox Proportional Hazards model using backwards elimination employing univariate cut-points to provide the prognostic model for the given population of colorectal cancer patients. In some embodiments, the TAPPS equation is (~−0.89*TEM1_Stroma)+(~0.62*COLIV_Tumor)+
   (~0.83*$FN$ stroma).

wherein coefficients A, B, and C are the coefficients derived for each respective marker in each respective tumor compartment in the multivariate Cox Proportional Hazards model using backwards elimination employing univariate cut-points to provide the prognostic model for the given population of colorectal cancer patients. It is understood to those of skill in the art that the coefficients of the TAPPS equation are subject to some variability depending upon the population of subjects diagnosed with colorectal cancer.

The subject's TAPPS score is then compared to the TAPPS score of a population of subjects diagnosed with colorectal cancer. The subject may be partitioned into a subgroup at any particular value(s) of the TAPPS score, where all patients with values in a given range can be classified as belonging to a particular risk group or group associated with a particular clinical outcome. The results of the analysis may be summarized in a report. This information is useful to the patient and the physician for assessing the risk versus benefit of observation versus adjuvant therapy for that patient. For example, if a subject is determined to be at high risk for recurrence of colorectal cancer, further therapy may be elected or administered. Such therapy may include TEM-1-targeted therapy (e.g., MORAb-004), chemotherapy, radiation therapy, and/or monitoring for disease recurrence or progression.

In some aspects, the methods for determining the risk that a subject diagnosed with colorectal cancer will develop a recurrence of colorectal cancer involve a) determining the level of expression for each marker of a panel of markers in a panel of tumor compartments in a tumor tissue sample from the subject, wherein the panel of markers comprises at least two of TEM1, HIF2α, CAIX, PDGFRβ, fibronectin, collagen I, collagen IV, and CD31 and wherein the panel of tumor compartments comprises at least three tumor compartments of pure stroma, tumor, stromal vessel, and tumor vessel; b) determining the subject's TAPPS score; and c) comparing the TAPPS score of the subject to the TAPPS score of a population of subjects diagnosed with colorectal cancer. The subject is assigned to the group at a low risk for recurrence of colorectal cancer if the subject's TAPPS score is low relative to the TAPPS score of the population. The subject is assigned to the group at a high risk for recurrence of colorectal cancer if the subject's TAPPS score is high relative to the TAPPS score of the population. In some aspects, if the subject's colorectal cancer is lymph node negative and the subject's TAPPS score is intermediate relative to the TAPPS score of the population, the subject is assigned to the low risk group for recurrence of colorectal cancer. In some aspects, if the subject's colorectal cancer is lymph node positive and the subject's TAPPS score is intermediate relative to the TAPPS score of the population, the subject is assigned to the high risk group for recurrence of colorectal cancer.

In some aspects, the methods of predicting clinical outcome for a subject diagnosed with colorectal cancer involve: a) determining the level of expression for each marker of a panel of markers in a panel of tumor compartments in a tumor tissue sample from the subject, wherein the panel of markers includes at least two of TEM1, HIF2α, CAIX, PDGFRβ, fibronectin, collagen I, collagen IV, and CD31 and wherein the panel of tumor compartments comprises at least three tumor compartments of pure stroma, tumor, stromal vessel, and tumor vessel; b) determining the subject's TAPPS score; and c) comparing the subject's TAPPS score to the TAPPS score of a population of subjects diagnosed with colorectal cancer. A low TAPPS score for the subject relative to the TAPPS score of the population is predictive of a positive clinical outcome. A high TAPPS score for the subject relative to the TAPPS score of the population is predictive of a poor clinical outcome. If the subject's colorectal cancer is lymph node negative, an intermediate TAPPS score of the subject relative to the TAPPS score for the population is predictive of a positive clinical outcome for the subject. If the subject's colorectal cancer is lymph node positive, an intermediate TAPPS score of the subject relative to the TAPPS score of the population is predictive of a poor clinical outcome for the subject. Clinical outcome may be expressed in terms of Progression-Free Survival (PFS), Recurrence-Free Interval (RFI), Overall Survival (OS), Disease-Free Survival (DFS), or Distant Recurrence-Free Interval (DRFI).

If a poor clinical outcome is predicted for the subject, the subject may elect or be subjected to further therapy, such as but not limited to TEM-1-targeted therapy (e.g., MORAb-004), chemotherapy, radiation therapy, and/or monitoring for disease recurrence or progression.

Also provided herein are methods of treatment of colorectal cancer wherein a subject determined by the disclosed methods to have high risk for recurrence of the colorectal cancer or for which a poor clinical outcome is predicted is administered therapy for the colorectal cancer, for example, TEM-1-targeted therapy, chemotherapy, and/or radiation therapy. Clinical application of the methods described herein would provide an objective assessment of a patient's likelihood of recurrence of the disease that is complementary to existing criteria. Based on this information, patients most likely to benefit from adjuvant therapy or from a more aggressive monitoring of disease recurrence can be identified. Conversely, patients who may be candidates for adjuvant therapy based on current prognostic criteria, but who are identified as being at low risk for recurrence based on this assay, may avoid the unnecessary risks associated with existing adjuvant therapy.

The methods described herein allow assignment of a subject diagnosed with colorectal cancer into a high risk for recurrence or a low risk for recurrence group or into a group predicted to have a positive clinical outcome or a group predicted to have a poor clinical outcome. The methods will assist patients and physicians in determining the need for adjuvant intervention or at least aggressive follow-up surveillance. The goal of the described methods is to improve the overall survival of the high risk patient group without exposing the remaining patients to the risks and costs associated with adjuvant therapy or monitoring for recurrence of disease. For example, a node negative patient identified by the methods herein as having a high risk test result might prompt that patient to choose adjuvant therapy.

Also described herein are computer-implemented methods for localizing a panel of markers within a colorectal cancer tumor tissue sample. In accordance with such methods, the tumor tissue sample (e.g., one or more sections thereof) is incubated with a panel of labels that specifically labels at least three tumor compartments of pure stroma, tumor, stromal vessel, and tumor vessel. The tumor tissue sample (e.g., one or more sections thereof) also is incubated with a panel of labels that labels a panel of markers comprising at least two of TEM1, HIF2α, CAIX, PDGFRβ, fibronectin, collagen I, collagen IV, and CD31. In some preferred embodiments, the panel of markers comprises four, five, six, seven, or all eight of TEM1, HIF2α, CAIX, PDGFRβ, fibronectin, collagen I, collagen IV, and CD31. In a preferred embodiment, the panel of markers comprises TEM1, HIF2α, CAIX, and PDGFRβ. In another preferred embodiment, the panel of markers comprises TEM1, HIF2α, CAIX, fibronectin, and PDGFRβ. In one embodiment the panel of marker includes TEM1, HIF2α, collagen IV, and fibronectin. A high resolution image of each of the labels in the tumor tissue sample is obtained using an optical imaging device. An image of the each of the tumor compartments and an image of each of the markers is generated. Pixel locations are then assigned to each of the tumor compartments based upon an intensity value of the label that specifically labels that tumor compartment at that pixel location. The images of each of the markers is then analyzed at the pixel locations assigned to each of the tumor compartments to identify those pixel locations having an intensity value indicative of the presence of the label for the marker, so as to thereby localize each marker of the panel of markers in the tumor tissue sample.

In some embodiments of the computer-implemented methods for localizing a panel of markers within a colorectal cancer tumor tissue sample, the tumor tissue sample is further incubated with a panel of labels that specifically labels two or more subcellular compartments of a cell nucleus, a cytoplasm, a nuclear membrane, a cellular membrane, a mitochondria, an endoplasmic reticulum, a peroxisome, and a lysosome. A high resolution image of each of the labels that specifically labels a subcellular compartment is then obtained using an optical imaging device to obtain an image of each of the subcellular compartments. Pixel locations are assigned to each of the subcellular compartments based upon an intensity value of the label that specifically labels that subcellular compartment at that pixel location.

In some aspects of the methods described herein (including the computer-implemented methods for localizing a panel of markers within a colorectal cancer tumor tissue sample, the methods of predicting clinical outcome for a subject diagnosed with colorectal cancer, the methods for determining the risk that a subject diagnosed with colorectal cancer will develop a recurrence of colorectal cancer, the methods for differential diagnosis, and the methods of treatment), the tissue sample is fixed, fixed and paraffin-embedded, fresh, and/or obtained from a biopsy. In some aspects, the colorectal cancer tumor tissue sample is a tissue microarray. In some embodiments, the tumor tissue sample has a thickness of about 5 microns.

In accordance with some embodiments of the disclosed methods, the colorectal cancer is lymph node negative or lymph node positive. In some aspects, the colorectal cancer is Stage I, Stage II, or Stage III cancer. The described methods may be carried out upon diagnosis of colorectal cancer, following surgical resection of the colorectal cancer, or following treatment for colorectal cancer, such as treatment with MORAb-004.

Labels employed by the methods described herein (including the computer-implemented methods for localizing a panel of markers within a colorectal cancer tumor tissue sample, the methods of predicting clinical outcome for a subject diagnosed with colorectal cancer, and the methods for determining the risk that a subject diagnosed with colorectal cancer will develop a recurrence of colorectal cancer) are readily known to those skilled in the art. For example, suitable labels include, but should not be considered limited to, antibodies (e.g., detectably labeled antibodies), radiolabels, fluorophores, fluorescent labels, epitope tags, biotin, chromophoric or chromogenic labels (e.g., 3,3-Diaminobenzidine), ECL labels, or enzymes. More specifically, the described labels include ruthenium, $^{111}$In-DOTA, $^{111}$In-diethylenetriaminepentaacetic acid (DTPA), horseradish peroxidase, alkaline phosphatase and beta-galactosidase, poly-histidine (HIS tag), acridine dyes, cyanine dyes, fluorone dyes, oxazin dyes, phenanthridine dyes, rhodamine dyes, Alexafluor® dyes, and the like. Examples of a fluorophore include 4',6-diamidino-2-phenylindole (DAPI), fluorescein isothiocyanate (FITC), or a cyanine dye (e.g., Cy 2, Cy3, Cy3B, Cy3.5, Cy5, Cy5.5, Cy7, and Cy7.5). In some embodiments, the label comprises an antibody labeled with a radiolabel, a fluorescent label, an epitope tag, biotin, a chromophore label, an ECL label, an enzyme, ruthenium, $^{111}$In-DOTA, $^{111}$In-diethylenetriaminepentaacetic acid (DTPA), horseradish peroxidase, alkaline phosphatase and beta-galactosidase, or poly-histidine or similar such labels known in the art. A signal amplification system (e.g., tyramide signal amplification) may be used with the label. The labels that define the tumor compartments may react with markers including but not limited to CD31, CD34, cytokeratin, beta catenin, alpha catenin and vimentin. In preferred embodiments, the label that reacts with any given tumor compartment marker or biomarker comprises an antibody.

Tissue Sample Arrays

Described herein are tissue sample arrays produced from cancerous tissue from one or more subjects, where the tissue samples are labeled with one or more antibodies that specifically binds to a cellular or extracellular protein that may have varied expression in a cancer cell. The described tissue samples in the array can be from a single subject or multiple subjects and may be from a single tumor or more than one tumor. For example, the described tissue array could be produced from multiple histological sections of a single tumor sample obtained from an individual subject. Alternatively, the cancerous tissue of the described array may be obtained from more than one tumor of a subject. In some embodiments where more than one tumor provides the histological samples for the array the tumors may be the same type, stage, or grade of tumor. The tissue samples of the array may be labeled with one or more antibodies in order to detect more or more cellular protein or an extracellular protein that have differential expression in cancer cells, or certain types of cancer cells than noncancerous cells. In some embodiments one or more tissue samples of the array may be labeled with more than one antibody, allowing for detection of more than one protein, where at least one of the labeled proteins does not have differential expression in a cancer cell.

The described tissue sample arrays may exist in a wide array of embodiments. In some embodiments the tissue sample arrays may be composed of multiple histological tumor samples each of which is labeled with at least one antibody that specifically binds to a protein that is known to be associated with a histological structure, such that the associated structure is labeled, where at least some tissue samples in the array are also labeled with at least one antibody that specifically binds to a different protein, which may or may not be a structural protein. In some embodiments the array samples may be labeled for structural proteins with one or more antibodies that specifically bind any one of cytokeratin, vimentin, and CD31, while the array samples may also be labeled with antibodies that specifically bind any one of TEM1, fibronectin-1, PDGFRβ, collagen I, collagen IV, HIF2α, or CAIX. In some embodiments the array samples may be labeled for structural proteins with one or more antibodies that specifically bind cytokeratin, vimentin, and CD31, while the array samples may also be labeled with antibodies that specifically bind TEM1, fibronectin, collagen IV, and HIF2α.

In some embodiments the described arrays may be prepared in such a way that each tissue sample in the array is labeled with a different combination of antibodies to allow for a variety of individual histological structures to be labeled across the array while these same tissue samples can be simultaneously labeled with one or more antibodies specific for different proteins, such that various protein expression profiles can be assessed across the array at the same time. Use of the array in this manner may allow a combination of parameters concerning the expression of proteins of interest to be obtained for a tissue or tumor of interest by making use of multiple query parameters across the array. For example, in one aspect, a single tissue sample in the array could be labeled to detect a protein of interest (such as TEM-1) and also be labeled to detect cytokeratin, vimentin and CD31 to denote certain cellular or histological structures of interest; furthermore other elements of the cell such as the nucleus, could be detected using a label capable of binding to DNA. On the same array other histological samples could be labeled in a similar manner, except that the label for TEM-1 could be replaced with a label for a different protein of interest, such as fibronectin-1, PDGFRβ, collagen I, collagen IV, HIF2α, or CAIX. One could then assess the expression levels of the labeled proteins of interest relative to one another and in relation to the labeled structural elements in each sample. Thus, one could determine, for example, the expression levels of any combination of TEM1, fibronectin-1, PDGFRβ, collagen I, collagen IV, HIF2α, and CAIX in a single tumor, assess the expression levels of these proteins relative to one another, and also determine the location of their expression relative to the labeled structural elements in each sample of the array. Detection of the labeled proteins may be achieved by immunohistochemical means. For example, fluorescence-based labeling, using a labeled primary antibody or a labeled secondary antibody, and detection using a fluorescence detector.

In view of the foregoing description, the following described embodiments may provide a further understanding of the tissue sample arrays disclosed herein. In one embodiment the described tissue sample array may include multiple histological slides of a tumor, where a majority of the histological slides are labeled to allow for the detection of the nuclei in cells of the tissue samples, detection of one or more of cytokeratin, vimentin, and CD31, and detection of one or more of TEM1, fibronectin-1, PDGFRβ, collagen I, collagen IV, HIF2α, and CAIX, where the labeled proteins are labeled in a manner to allow for their localization and quantitation in cells of the histological slides. In one embodiment the described tissue sample array may include multiple histological slides of a tumor, where a majority of the histological slides are labeled to allow for the detection of the nuclei of cells in the tissue samples, detection of one or more of cytokeratin, vimentin, and CD31, and at least one cell labeled with any one or more of cytokeratin, vimentin, and CD31 is also labeled with one or more antibodies specific for TEM1, fibronectin-1, PDGFRβ, collagen I, collagen IV, HIF2α, or CAIX, where the labeled proteins are labeled in a manner to allow for their localization and quantitation in cells of the histological slides.

In one embodiment the described tissue sample array may include multiple histological slides of a tumor, where a majority of the histological slides are labeled to allow for: the detection of the nuclei of cells in the tissue samples, detection of one or more of cytokeratin, vimentin, and CD31, and at least one histological slide labeled with an antibody specific for one or more of cytokeratin, vimentin, and CD31 is also labeled with one antibody specific for TEM1, fibronectin-1, PDGFRβ, collagen I, collagen IV, HIF2α, or CAIX, such that the array as a whole includes at least one histological slide labeled with any one or more of cytokeratin, vimentin, and CD31 is also labeled with one antibody specific for TEM1, at least one histological slide labeled with any one or more of cytokeratin, vimentin, and CD31 is also labeled with one antibody specific for fibronectin-1, at least one histological slide labeled with any one or more of cytokeratin, vimentin, and CD31 is also labeled with one antibody specific for PDGFRβ, at least one histological slide labeled with any one or more of cytokeratin, vimentin, and CD31 is also labeled with one antibody specific for collagen I, at least one histological slide labeled with any one or more of cytokeratin, vimentin, and CD31 is also labeled with one antibody specific for collagen IV, at least one histological slide labeled with any one or more of cytokeratin, vimentin, and CD31 is also labeled with one antibody specific for HIF2α, and at least one histological slide labeled with any one or more of cytokeratin, vimentin, and CD31 is also labeled with one antibody specific for CAIX, where the labeled proteins are labeled in a manner to allow for their localization and quantitation in cells of the histological slides.

In one embodiment the described tissue sample array may include multiple histological slides of a tumor, where a majority of the histological slides are labeled to allow for: the detection of the nuclei of cells in the tissue samples, detection of one or more of cytokeratin, vimentin, and CD31, and at least one histological slide labeled with any one or more of cytokeratin, vimentin, and CD31 is also labeled with one antibody specific for TEM1, fibronectin-1, PDGFRβ, collagen I, collagen IV, HIF2α, or CAIX, such that the array as a whole includes at least one histological slide labeled with: an antibody specific for vimentin and is also labeled with one antibody specific for TEM1; an antibody specific for cytokeratin and is also labeled with one antibody specific for TEM1; an antibody specific for vimentin, an antibody specific for CD31, and is also labeled with one antibody specific for TEM1; an antibody specific for cytokeratin, an antibody specific for CD31, and is also labeled with one antibody specific for TEM1; an antibody specific for vimentin, an antibody specific for CD31, and is also labeled with one antibody specific for HIF2α; an antibody specific for vimentin, and is also labeled with one antibody specific for HIF2α; an antibody specific for cytokeratin and is also labeled with one antibody specific for CAIX; an antibody specific for cytokeratin, an antibody specific for CD31, and is also labeled with one antibody specific for CAIX; an antibody specific for vimentin and is also labeled with one antibody specific for PDGFRβ; an antibody specific for vimentin, an antibody specific for CD31, and is also labeled with one antibody specific for PDGFRβ; an antibody specific for vimentin and is also labeled with one antibody specific for fibronectin-1; an antibody specific for vimentin and is also labeled with one antibody specific for collagen I;

an antibody specific for vimentin, an antibody specific for CD31, and is also labeled with one antibody specific for collagen I; an antibody specific for vimentin and is also labeled with one antibody specific for collagen IV; and an antibody specific for vimentin, an antibody specific for CD31, and is also labeled with one antibody specific for collagen IV.

In one embodiment the described tissue sample array may include multiple histological slides of a tumor, where a majority of the histological slides are labeled to allow for: the detection of the nuclei of cells in the tissue samples, detection of one or more of cytokeratin, vimentin, and CD31, and at least one histological slide labeled with any one or more of cytokeratin, vimentin, and CD31 is also labeled with one antibody specific for TEM1, fibronectin-1, PDGFRβ, collagen I, collagen IV, HIF2α, or CAIX, such that the array as a whole includes at any one or more of the following labeling combinations: an antibody specific for vimentin and is also labeled with one antibody specific for TEM1; an antibody specific for cytokeratin and is also labeled with one antibody specific for TEM1; an antibody specific for vimentin, an antibody specific for CD31, and is also labeled with one antibody specific for TEM1; an antibody specific for cytokeratin, an antibody specific for CD31, and is also labeled with one antibody specific for TEM1; an antibody specific for vimentin, an antibody specific for CD31, and is also labeled with one antibody specific for HIF2α; an antibody specific for vimentin, and is also labeled with one antibody specific for HIF2α; an antibody specific for cytokeratin and is also labeled with one antibody specific for CAIX; an antibody specific for cytokeratin, an antibody specific for CD31, and is also labeled with one antibody specific for CAIX; an antibody specific for vimentin and is also labeled with one antibody specific for PDGFRβ, an antibody specific for vimentin, an antibody specific for CD31, and is also labeled with one antibody specific for PDGFRβ; an antibody specific for vimentin and is also labeled with one antibody specific for fibronectin-1; an antibody specific for vimentin and is also labeled with one antibody specific for collagen I; an antibody specific for vimentin, an antibody specific for CD31, and is also labeled with one antibody specific for collagen I; an antibody specific for vimentin and is also labeled with one antibody specific for collagen IV; or an antibody specific for vimentin, an antibody specific for CD31, and is also labeled with one antibody specific for collagen IV.

In one embodiment the described tissue sample array may include multiple histological slides of a tumor, where a majority of the histological slides are labeled to allow for: the detection of the nuclei of cells in the tissue samples, detection of one or more of cytokeratin, vimentin, and CD31, and at least one histological slide labeled with any one or more of cytokeratin, vimentin, and CD31 is also labeled with one antibody specific for TEM1, fibronectin-1, PDGFRβ, collagen I, collagen IV, HIF2α, or CAIX, such that the array as a whole includes at least one histological slide labeled with: an antibody specific for vimentin and is also labeled with one antibody specific for TEM1; an antibody specific for cytokeratin, an antibody specific for CD31, and is also labeled with one antibody specific for TEM1; an antibody specific for vimentin, an antibody specific for CD31, and is also labeled with one antibody specific for HIF2α; an antibody specific for vimentin, and is also labeled with one antibody specific for HIF2α; an antibody specific for cytokeratin and is also labeled with one antibody specific for CAIX; an antibody specific for cytokeratin, an antibody specific for CD31, and is also labeled with one antibody specific for CAIX; an antibody specific for vimentin, an antibody specific for CD31, and is also labeled with one antibody specific for PDGFRβ; and an antibody specific for vimentin and is also labeled with one antibody specific for fibronectin-1.

In one embodiment the described tissue sample array may include multiple histological slides of a tumor, where a majority of the histological slides are labeled to allow for: the detection of the nuclei of cells in the tissue samples, detection of one or more of cytokeratin, vimentin, and CD31, and at least one histological slide labeled with any one or more of cytokeratin, vimentin, and CD31 is also labeled with one antibody specific for TEM1, fibronectin-1, PDGFRβ, collagen I, collagen IV, HIF2α, or CAIX, such that the array as a whole includes at least one histological slide labeled with: an antibody specific for vimentin and is also labeled with one antibody specific for TEM1; an antibody specific for cytokeratin, an antibody specific for CD31, and is also labeled with one antibody specific for TEM1; an antibody specific for vimentin, an antibody specific for CD31, and is also labeled with one antibody specific for HIF2α; an antibody specific for cytokeratin, an antibody specific for CD31, and is also labeled with one antibody specific for CAIX; an antibody specific for vimentin, an antibody specific for CD31, and is also labeled with one antibody specific for PDGFRβ; and an antibody specific for vimentin and is also labeled with one antibody specific for fibronectin-1.

In one embodiment the described tissue sample array may include multiple histological slides of a tumor, where a majority of the histological slides are labeled to allow for: the detection of the nuclei of cells in the tissue samples, detection of one or more of cytokeratin, vimentin, and CD31, and at least one histological slide labeled with any one or more of cytokeratin, vimentin, and CD31 is also labeled with one antibody specific for TEM1, fibronectin-1, PDGFRβ, collagen I, collagen IV, HIF2α, or CAIX, such that the array as a whole includes from 2 to 5 histological slides labeled with: an antibody specific for vimentin and is also labeled with one antibody specific for TEM1; an antibody specific for cytokeratin, an antibody specific for CD31, and is also labeled with one antibody specific for TEM1; an antibody specific for vimentin, an antibody specific for CD31, and is also labeled with one antibody specific for HIF2α; an antibody specific for vimentin, and is also labeled with one antibody specific for HIF2α; an antibody specific for cytokeratin and is also labeled with one antibody specific for CAIX; an antibody specific for cytokeratin, an antibody specific for CD31, and is also labeled with one antibody specific for CAIX; an antibody specific for vimentin, an antibody specific for CD31, and is also labeled with one antibody specific for PDGFRβ; and an antibody specific for vimentin and is also labeled with one antibody specific for fibronectin-1.

In one embodiment the described tissue sample array may include multiple histological slides of a tumor, where a majority of the histological slides are labeled to allow for: the detection of the nuclei of cells in the tissue samples, detection of one or more of cytokeratin, vimentin, and CD31, and at least one histological slide labeled with any one or more of cytokeratin, vimentin, and CD31 is also labeled with one antibody specific for TEM1, fibronectin-1, PDGFRβ, collagen I, collagen IV, HIF2α, or CAIX, such that the array as a whole includes from 2 to 5 histological slides labeled with: an antibody specific for vimentin and is also labeled with one antibody specific for TEM1; an antibody specific for cytokeratin, an antibody specific for CD31, and is also labeled with one antibody specific for TEM1; an antibody specific for vimentin, an antibody specific for CD31, and is also labeled with one antibody specific for HIF2α; an antibody specific for cytokeratin, an antibody specific for CD31, and is also labeled with one antibody specific for CAIX; an antibody specific for vimentin, an antibody specific for CD31, and is also labeled with one antibody specific for PDGFRβ; and an antibody specific for vimentin and is also labeled with one antibody specific for fibronectin-1.

In one embodiment the described tissue sample array may include multiple histological slides of a tumor, where a majority of the histological slides are labeled to allow for: the detection of the nuclei of cells in the tissue samples, detection of one or more of cytokeratin, vimentin, and CD31, and at least one histological slide labeled with any one or more of cytokeratin, vimentin, and CD31 is also labeled with one antibody specific for TEM1, fibronectin-1, PDGFRβ, collagen I, collagen IV, HIF2α, or CAIX, such that the array as a whole includes only histological slides labeled with: an antibody specific for vimentin and is also labeled with one antibody specific for TEM1; an antibody specific for cytokeratin, an antibody specific for CD31, and is also labeled with one antibody specific for TEM1; an antibody specific for vimentin, an antibody specific for CD31, and is also labeled with one antibody specific for HIF2α; an antibody specific for vimentin, and is also labeled with one antibody specific for HIF2α; an antibody specific for cytokeratin and is also labeled with one antibody specific for CAIX; an antibody specific for cytokeratin, an antibody specific for CD31, and is also labeled with one antibody specific for CAIX; an antibody specific for vimentin, an antibody specific for CD31, and is also labeled with one antibody specific for PDGFRβ; and an antibody specific for vimentin and is also labeled with one antibody specific for fibronectin-1.

In one embodiment the described tissue sample array may include multiple histological slides of a tumor, where a majority of the histological slides are labeled to allow for: the detection of the nuclei of cells in the tissue samples, detection of one or more of cytokeratin, vimentin, and CD31, and at least one histological slide labeled with any one or more of cytokeratin, vimentin, and CD31 is also labeled with one antibody specific for TEM1, fibronectin-1, PDGFRβ, collagen I, collagen IV, HIF2α, or CAIX, such that the array as a whole includes only histological slides labeled with: an antibody specific for vimentin and is also labeled with one antibody specific for TEM1; an antibody specific for cytokeratin, an antibody specific for CD31, and is also labeled with one antibody specific for TEM1; an antibody specific for vimentin, an antibody specific for CD31, and is also labeled with one antibody specific for HIF2α; an antibody specific for cytokeratin, an antibody specific for CD31, and is also labeled with one antibody specific for CAIX; an antibody specific for vimentin, an antibody specific for CD31, and is also labeled with one antibody specific for PDGFRβ; and an antibody specific for vimentin and is also labeled with one antibody specific for fibronectin-1.

In one embodiment the described tissue sample array may include multiple histological slides of a tumor, where a majority of the histological slides are labeled to allow for: the detection of the nuclei of cells in the tissue samples, detection of one or more of cytokeratin, vimentin, and CD31, and at least one histological slide labeled with any one or more of cytokeratin, vimentin, and CD31 is also labeled with one antibody specific for TEM1, fibronectin-1, PDGFRβ, collagen I, collagen IV, HIF2α, or CAIX, such that the array as a whole includes histological slides labeled with only: an antibody specific for vimentin and is also labeled with one antibody specific for TEM1; an antibody specific for cytokeratin, an antibody specific for CD31, and is also labeled with one antibody specific for TEM1; an antibody specific for vimentin, an antibody specific for CD31, and is also labeled with one antibody specific for HIF2α; an antibody specific for vimentin, and is also labeled with one antibody specific for HIF2α; an antibody specific for cytokeratin and is also labeled with one antibody specific for CAIX; an antibody specific for cytokeratin, an antibody specific for CD31, and is also labeled with one antibody specific for CAIX; an antibody specific for vimentin, an antibody specific for CD31, and is also labeled with one antibody specific for PDGFRβ; and an antibody specific for vimentin and is also labeled with one antibody specific for fibronectin-1.

In one embodiment the described tissue sample array may include multiple histological slides of a tumor, where a majority of the histological slides are labeled to allow for: the detection of the nuclei of cells in the tissue samples, detection of one or more of cytokeratin, vimentin, and CD31, and at least one histological slide labeled with any one or more of cytokeratin, vimentin, and CD31 is also labeled with one antibody specific for TEM1, fibronectin-1, PDGFRβ, collagen I, collagen IV, HIF2α, or CAIX, such that the array as a whole includes histological slides labeled with only: an antibody specific for vimentin and is also labeled with one antibody specific for TEM1; an antibody specific for cytokeratin, an antibody specific for CD31, and is also labeled with one antibody specific for TEM1; an antibody specific for vimentin, an antibody specific for CD31, and is also labeled with one antibody specific for HIF2α; an antibody specific for cytokeratin, an antibody specific for CD31, and is also labeled with one antibody specific for CAIX; an antibody specific for vimentin, an antibody specific for CD31, and is also labeled with one antibody specific for PDGFRβ; and an antibody specific for vimentin and is also labeled with one antibody specific for fibronectin-1.

In one embodiment the described tissue sample array may include multiple histological slides of a tumor, where a majority of the histological slides are labeled to allow for: the detection of the nuclei of cells in the tissue samples, detection of one or more of cytokeratin, vimentin, and CD31, and at least one histological slide labeled with any one or more of cytokeratin, vimentin, and CD31 is also labeled with one antibody specific for TEM1, fibronectin-1, PDGFRβ, collagen I, collagen IV, HIF2α, or CAIX, such that the array as a whole includes histological slides labeled with only: an antibody specific for vimentin and is also labeled with one antibody specific for TEM1; an antibody specific for cytokeratin, an antibody specific for CD31, and is also labeled with one antibody specific for TEM1; an antibody specific for vimentin, an antibody specific for CD31, and is also labeled with one antibody specific for HIF2α an antibody specific for cytokeratin and is also labeled with one antibody specific for collagen IV; and an antibody specific for vimentin and is also labeled with one antibody specific for fibronectin-1.

As will be appreciated by those skilled in the art, other embodiments of the antigen detection parameters defined herein could also be employed to yield substantially similar results to those provided by the described methods or tissue arrays. For example, one could simply combine certain labeling conditions described separately above, but use distinct detection conditions to avoid interference that would otherwise be caused by the addition labels. Other such modifications known to those skilled in the art could also be used in an attempt to avoid the described detection methods; however, such alternatives should be considered within the knowledge of the skilled artisan when considered in view of the present disclosure.

Kits

The materials for use in the methods of the present invention are suited for preparation of kits produced in accordance with well-known procedures. The invention thus provides kits comprising agents for detecting and/or quantitating the expression of the disclosed panel of markers for predicting prognostic outcome, which may include labels specific for the panel of markers, for example, at least two labels of a label specific for TEM1, a label specific for PDGFRβ, a label specific for HIF2α, a label specific for CAIX, a label specific for fibronectin, a label specific for collagen I, a label specific for collagen IV, and a label specific for CD31. The label specific for TEM1 may include an antibody directed against TEM1, for example, antibody 9G5 (antibody-producing cells producing the 9G5 antibody have been deposited with the American Type Culture Collection, 10801 University Blvd., Manassas, Va. 20110-2209, on Feb. 16, 2012 and have been assigned ATCC Accession No. PTA-12547). The label specific for PDGFRβ may include an antibody directed against PDGFRβ. The label specific for HIF2α may include an antibody directed against HIF2α. The label specific for CAIX may include an antibody directed against CAIX. The label specific for fibronectin may include an antibody directed against fibronectin. The label specific for collagen I may include an antibody directed against collagen I. The label specific for collagen IV may include an antibody directed against collagen IV. The labels that define the tumor compartments may react with markers including but not limited to CD31, CD34, cytokeratin, beta catenin, alpha catenin and vimentin. Labels for the biomarkers and tumor compartment markers are readily known to those skilled in the art. For example, suitable labels include, but should not be considered limited to, antibodies (e.g., a detectably labeled antibody), radiolabels, fluorophores, fluorescent labels, epitope tags, biotin, chromophoric or chromogenic labels (e.g., 3,3-Diaminobenzidine), ECL labels, or enzymes. More specifically, the described labels include ruthenium, $^{111}$In-DOTA, $^{111}$In-diethylenetriaminepentaacetic acid (DTPA), horseradish peroxidase, alkaline phosphatase and beta-galactosidase, poly-histidine (HIS tag), acridine dyes, cyanine dyes, fluorone dyes, oxazin dyes, phenanthridine dyes, rhodamine dyes, Alexafluor® dyes, and the like. Examples of a fluorophore include 4',6-diamidino-2-phenylindole (DAPI), fluorescein isothiocyanate (FITC), or a cyanine dye (e.g., Cy 2, Cy3, Cy3B, Cy3.5, Cy5, Cy5.5, Cy7, and Cy7.5). In some embodiments, the label comprises an antibody labeled with a radiolabel, a fluorescent label, an epitope tag, biotin, a chromophore label, an ECL label, an enzyme, ruthenium, $^{111}$In-DOTA, $^{111}$In-diethylenetriaminepentaacetic acid (DTPA), horseradish peroxidase, alkaline phosphatase and beta-galactosidase, or poly-histidine or similar such labels known in the art. A signal amplification system (e.g., tyramide signal amplification) may be used with the label and thus included in the described kits.

In addition, the kits may optionally comprise the reagent(s) with an identifying description or label or instructions relating to their use in the methods described herein. The kits may comprise containers, each with one or more of the various reagents (typically in concentrated form) utilized in the methods. Mathematical algorithms used to estimate or quantify prognostic or predictive information are also properly potential components of kits.

In some aspects are provided a kit for localizing or quantifying a panel of markers in colorectal cancer including a label specific for TEM1, a label specific for PDGFRβ, a label specific for HIF2α, and a label specific for CAIX. In some embodiments, instructions for using the kit are included.

In some aspects are provided a kit for localizing or quantifying a panel of markers in colorectal cancer including a label specific for TEM1, a label specific for collagen IV, a label specific for HIF2α, and a label specific for fibronectin-1. In some embodiments, instructions for using the kit are included.

The kits described herein also may include one or more of a label specific for cell nuclei, a label specific for tumor cytoplasm, a label specific for tumor stroma, a label specific for vasculature, a label for tumor vasculature, and a label for tumor stromal vasculature. For example, the label specific for tumor cytoplasm may react with cytokeratin, the label specific for tumor stroma may react with vimentin, and the label specific for vasculature may react with CD31.

In some embodiment of the described kits, the label specific for TEM1 comprises an antibody directed against TEM1, the label specific for PDGFRβ comprises an antibody directed against PDGFRβ, the label specific for HIF2α comprises an antibody directed against HIF2α, the label specific for CAIX comprises an antibody directed against CAIX, the label specific for fibronectin comprises an antibody directed against fibronectin, the label specific for collagen I comprises an antibody directed against collagen I, and the label specific for collagen IV comprises an antibody directed against collagen IV.

Reports

The methods described herein may produce a report or summary of the likelihood of recurrence of colorectal cancer, the prediction of the clinical outcome, or the localization or the markers. The described methods and reports can further include storing the report in a database. Alternatively, the methods can further create a record in a database for the subject and populate the record with data. In one embodiment the report is a paper report, in another embodiment the report is an auditory report, in another embodiment the report is an electronic record. It is contemplated that the report is provided to a physician and/or the patient. The receiving of the report can further include establishing a network connection to a server computer that includes the data and report and requesting the data and report from the server computer.

Selected Aspects

Selected aspects of the subject matter described herein are provided to exemplify how the described subject matter may be used or applied. These selected aspects are provided by way of illustration, and are not intended to limit the present disclosure in any way.

The following aspects are provided:

1. A method for determining the risk that a subject diagnosed with colorectal cancer will develop a recurrence of colorectal cancer comprising: a) determining the level of expression for each marker of a panel of markers in a panel of tumor compartments in a tumor tissue sample from the subject, wherein the panel of markers comprises at least two of TEM1, HIF2α, CAIX, PDGFRβ, fibronectin, collagen I, collagen IV, and CD31 and wherein the panel of tumor compartments comprises at least three tumor compartments of pure stroma, tumor, stromal vessel, and tumor vessel; b) determining the TAPPS score for said subject; and c) comparing the TAPPS score of the subject to the TAPPS score of a population of subjects diagnosed with colorectal cancer, wherein the subject is at a low risk for recurrence of colorectal cancer if the subject's TAPPS score is low relative to the TAPPS score of the population and wherein the subject is at a high risk for recurrence of colorectal cancer if the subject's TAPPS score is high relative to the TAPPS score of the population.

2. The method of aspect 1, wherein the level of expression for each marker of the panel of markers is determined using an automated pathology system.

3. The method of aspect 1 or 2, wherein the level of expression for each marker of the panel of markers is determined using a quantitative image analysis procedure.

4. The method of any one of aspects 1 to 3, wherein the colorectal cancer is lymph node negative.

5. The method of aspect 4, wherein the subject is at low risk for recurrence of colorectal cancer if the subject's TAPPS score is intermediate relative to the TAPPS score of the population.

6. The method of any one of aspects 1 to 3, wherein the colorectal cancer is lymph node positive.

7. The method of aspect 6, wherein the subject is at high risk for recurrence of colorectal cancer if the subject's TAPPS score is intermediate relative to the TAPPS score of the population.

8. The method of any one previous aspect, wherein the colorectal cancer is Stage I, Stage II, or Stage III cancer.

9. The method of any one previous aspect further comprising identifying the at least three compartments in the tumor tissue sample from the subject.

10. The method of any one previous aspect further comprising identifying at least one of tumor cell nuclei and tumor cell cytoplasm.

11. The method of any previous aspect wherein said panel of markers comprises three of TEM1, HIF2α, CAIX, PDGFRβ, fibronectin, collagen I, collagen IV, and CD31

12. The method of any one previous aspect wherein said panel of markers comprises four of TEM1, HIF2α, CAIX, PDGFRβ, fibronectin, collagen I, collagen IV, and CD31.

13. The method of any one of aspects 1 to 10 wherein said panel of markers comprises five of TEM1, HIF2α, CA9, PDGFRβ, fibronectin, collagen I, collagen IV, and CD31.

14. The method of any one of aspects 1 to 10 wherein said panel of markers comprises six of TEM1, HIF2α, CAIX, PDGFRβ, fibronectin, collagen I, collagen IV, and CD31.

15. The method of any one of aspects 1 to 10 wherein said panel of markers comprises TEM1 and CAIX.

16. The method of aspect 12 wherein said panel of markers comprises TEM1, HIF2α, CAIX, and PDGFRβ.

17. The method of aspect 13 wherein said panel of markers comprises TEM1, HIF2α, CAIX, fibronectin, and PDGFRβ.

18. The method of any one of aspects 1 to 10 wherein said panel of markers comprises TEM1, HIF2α, fibronectin, and collagen IV.

19. The method of any previous aspect wherein the panel of tumor compartments comprises one or more of stroma and tumor.

20. The method of any one of aspects 1 to 19 wherein the panel of tumor compartments comprises one or more of stroma, tumor, stromal vessel, and tumor vessel.

21. The method of any previous aspect wherein step a) comprises determining the expression level of TEM1 in tumor stroma, determining the level of TEM1 in tumor vessel, determining the level of CAIX in tumor vessel, and determining the level of CAIX in tumor.

22. The method of any one of aspects 1 to 20 wherein step a) comprises determining the expression level of TEM1 in tumor stroma, determining the level of TEM1 in tumor vessel, determining the expression level of HIF2α in stroma vessel, determining the level of HIF2α in tumor stroma, determining the level of CAIX in tumor, determining the level of CAIX in tumor vessel, determining the level of PDGFRβ in tumor stroma.

23 The method of aspect 22 wherein step a) further comprises determining the expression level of fibronectin in tumor stroma.

24. The method of any one previous aspect, further comprising the step of creating a report summarizing said risk.

25. The method of any one previous aspect, wherein, if said subject is determined to be at high risk for recurrence of colorectal cancer, said subject is subjected to further therapy.

26. The method of aspect 25, wherein said further therapy comprises TEM-1-targeted therapy, chemotherapy, and/or radiation therapy.

27. The method of aspect 26 wherein said TEM-1-targeted therapy comprises MORAb-004.

28. The method of any one previous aspect, wherein, if said subject is determined to be at high risk for recurrence of colorectal cancer, said subject is subjected to monitoring for disease recurrence or progression.

29. The method of any one previous aspect, wherein tumor tissue sample is fixed and paraffin-embedded.

30. The method of any one previous aspect, wherein tumor tissue sample is fresh.

31. The method of any one previous aspect, wherein tumor tissue sample is obtained from a tissue biopsy.

32. The method of any one previous aspect, wherein said subject is a human.

33. The method of aspect 1 wherein the TAPPS equation is determined by determining the coefficients A, B, C, D, etc. for each of the markers in each of the tumor compartments selected for inclusion for the population of colorectal cancer patients.

34. The method of aspect 1 wherein the TAPPS equation is determined by determining the coefficients A, B, C, and D for the population of colorectal cancer patients to provide any one of the following TAPPS equations:

(~$A$*TEM1_Stroma)+
(~$B$*TEM1_TumorVasculature)+
(~$C$*CAIX_TumorVasculature)+
(~$D$*CAIX_Tumor)

(~$A$*TEM1_Stroma)+
(~$B$*TEM1_TumorVasculature)+
(~$C$*HIF2α_StromaVasculature)+
(~$D$*COLIV_Tumor)+(~$E$*$FN$ stroma), or (~$A$*TEM1_Stroma)+(~$B$*COLIV_Tumor)+(~$C$*$FN$ stroma), and by determining the TAPPS score of the subject using said TAPP equation.

35. The method of aspect 1 wherein the TAPPS equation is determined by determining coefficients A, B, C, D, E, F, G, and H for the population of colorectal cancer patients to provide the TAPPS equation:

(~$A$*TEM1_Stroma)+
(~$B$*TEM1_TumorVasculature)+
(~$C$*HIF2α_StromaVasculature)+
(~$D$*HIF2α_Stroma)+
(~$E$*CAIX_TumorVasculature)+
(~$F$*CAIX_Tumor)+(~$G$*PDGFRβ_Stroma)+
(~$H$*Fibronectin_Stroma)

and by determining the TAPPS score of the subject using said TAPPS equation.

36. The method of aspect 1 wherein the TAPPS score of the subject is determined using any one of the following TAPPS equations:

(~–1.063*TEM1_Stroma)+
(~0.478*TEM1_TumorVasculature)+(~–
1.095*HIF2α_StromaVasculature)+
(~0.407*HIF2α_Stroma)+(~–
1.096*CAIX_TumorVasculature)+
(~0.912*CAIX_Tumor)+
(~0.600*PDGFRβ_Stroma)+
(~0.714*Fibronectin_Stroma), (~–0.89*TEM1_Stroma)+
(~–1.19*TEM1_TumorVasculature)+(~–
0.76*HIF2α_StromaVasculature)+(~0.62*CO-
LIV_Tumor)+(~0.83*$FN$ stroma)

or (~–0.89*TEM1_Stroma)+(~0.62*COLIV_Tumor)+
(~0.83*$FN$ stroma).

37. A method of predicting clinical outcome for a subject diagnosed with colorectal cancer, comprising: a) determining the level of expression for each marker of a panel of markers in a panel of tumor compartments in a tumor tissue sample from the subject, wherein the panel of markers comprises at least two of TEM1, HIF2α, CAIX, PDGFRβ, fibronectin, collagen I, collagen IV, and CD31 and wherein the panel of tumor compartments comprises at least three tumor compartments of pure stroma, tumor, stromal vessel, and tumor vessel; b) determining the TAPPS score for said subject; and c) comparing the TAPPS score of the subject to the TAPPS score of a population of subjects diagnosed with colorectal cancer; wherein a low TAPPS score for said subject relative to the TAPPS score of the population is predictive of a positive clinical outcome and wherein a high TAPPS score for said subject relative to the TAPPS score of the population is predictive of a poor clinical outcome.

38. The method of aspect 37, wherein the level of expression for each marker of the panel of markers is determined using an automated pathology system.

39. The method of aspect 37 or 38, wherein the level of expression for each marker of the panel of markers is determined using a quantitative image analysis procedure.

40. The method of any one of aspects 37 to 39, wherein the colorectal cancer is lymph node negative.

41. The method of aspect 34, wherein an intermediate TAPPS score for said subject relative to the TAPPS score of the population is predictive of a positive clinical outcome for said subject.

42. The method of any one of aspects 37 to 39, wherein the colorectal cancer is lymph node positive.

43. The method of aspect 42, wherein an intermediate TAPPS score for said subject relative to the TAPPS score of the population is predictive of a poor clinical outcome for said subject.

44. The method of any one of aspects 37 to 43, wherein the colorectal cancer is Stage I, Stage II, or Stage III cancer.

45. The method of any one of aspects 37 to 44, further comprising identifying the at least two compartments in the tumor tissue sample from the subject.

46. The method of any one of aspects 37 to 45, further comprising identifying at least one of tumor cell nuclei and tumor cell cytoplasm.

47. The method of any one of aspects 37 to 46 wherein said panel of markers comprises three of TEM1, HIF2α, CAIX, PDGFRβ, fibronectin, collagen I, collagen IV, and CD31.

48. The method of any one of aspects 37 to 46, wherein said panel of markers comprises four of TEM1, HIF2α, CAIX, PDGFRβ, fibronectin, collagen I, collagen IV, and CD31.

49. The method of any one of aspects 37 to 46, wherein said panel of markers comprises five of TEM1, HIF2α, CAIX, PDGFRβ, fibronectin, collagen I, collagen IV, and CD31.

50. The method of any one of aspects 37 to 46, wherein said panel of markers comprises six of TEM1, HIF2α, CAIX, PDGFRβ, fibronectin, collagen I, collagen IV, and CD31.

51. The method of aspect 48 wherein said panel of markers comprises TEM1, HIF2α, collagen IV, and fibronectin.

52. The method of aspect 51 wherein said panel of tumor compartments comprises either of a) stroma, tumor vessel, stroma vessel, and tumor or b) stroma and tumor.
53. The method of aspect 48, wherein said panel of markers comprises TEM1, HIF2α, CAIX, and PDGFRβ.
54. The method of aspect 49, wherein said panel of markers comprises TEM1, HIF2α, CAIX, fibronectin, and PDGFRβ.
55. The method of any one of aspects 37 to 46, wherein said panel of markers comprises TEM1, HIF2α, CAIX, PDGFRβ, fibronectin, collagen I, collagen IV, and CD31.
56. The method of any one of aspects 37 to 55, wherein the panel of tumor compartments comprises pure stroma, tumor, stromal vessel, and tumor vessel.
57. The method of any one of aspects 37 to 56, wherein step a) comprises determining the expression level of TEM1 in tumor stroma, determining the level of TEM1 in tumor vessel, determining the expression level of HIF2α in stroma vessel, determining the level of HIF2α in tumor stroma, determining the level of CAIX in tumor, determining the level of CAIX in tumor vessel, and determining the level of PDGFRβ in tumor stroma.
58. The method of aspect 57 wherein step a) further comprises determining the expression level of fibronectin in tumor stroma.
59. The method of any one of aspects 37 to 58, further comprising the step of creating a report summarizing said prediction.
60. The method of any one of aspects 37 to 59, wherein, if a poor clinical outcome is predicted for said subject, said subject is subjected to further therapy.
61. The method of aspect 60, wherein said further therapy comprises TEM-1-targeted therapy, chemotherapy, and/or radiation therapy.
62. The method of aspect 61 wherein said TEM-1-targeted therapy comprises MORAb-004.
63. The method of any one of aspects 37 to 62, wherein, if a poor clinical outcome is predicted for said subject, said subject is subjected to monitoring for disease recurrence or progression.
64. The method of any one of aspects 37 to 63, wherein tumor tissue sample is fixed and paraffin-embedded.
65. The method of any one of aspects 37 to 64, wherein tumor tissue sample is fresh.
66. The method of any one of aspects 37 to 65, wherein tumor tissue sample is obtained from a tissue biopsy.
67. The method of any one of aspects 37 to 66, wherein said subject is a human.
68. The method of any one of aspects 37 to 67, wherein said clinical outcome is expressed in terms of Progression-Free Survival (PFS), Recurrence-Free Interval (RFI), Overall Survival (OS), Disease-Free Survival (DFS), or Distant Recurrence-Free Interval (DRFI).
69. The method of aspect 37 wherein the TAPPS equation is determined by determining the coefficients A, B, C, D, etc. for each of the markers in each of the tumor compartments selected for inclusion for the population of colorectal cancer patients.
70. The method of aspect 37 wherein the TAPPS equation is determined by determining the coefficients A, B, C, and for the population of colorectal cancer patients to provide the TAPPS equation:

$$(\sim A*TEM1\_Stroma)+$$
$$(\sim B*TEM1\_TumorVasculature)+$$
$$(\sim C*CAIX\_TumorVasculature)+$$
$$(\sim D*CAIX\_Tumor)$$

and by determining the TAPPS score of the subject using said TAPP equation.

71. The method of aspect 37, herein the TAPPS equation is determined by determining coefficients A, B, C, D, E, F, G, and H for the population of colorectal cancer patients to provide the TAPPS equation:

$$(\sim A*TEM1\_Stroma)+$$
$$(\sim B*TEM1\_TumorVasculature)+$$
$$(\sim C*HIF2\alpha\_StromaVasculature)+$$
$$(\sim D*HIF2\alpha\_Stroma)+$$
$$(\sim E*CAIX\_TumorVasculature)+$$
$$(\sim F*CAIX\_Tumor)+(\sim G*PDGFR\beta\_Stroma)+$$
$$(\sim H*Fibronectin\_Stroma)$$

and by determining the TAPPS score of the subject using said TAPPS equation.

72. The method of aspect 37, wherein the TAPPS score of the subject is determined using the following TAPPS equation:

$$(\sim -1.063*TEM1\_Stroma)+$$
$$(\sim 0.478*TEM1\_TumorVasculature)+(\sim -1.095*HIF2\alpha\_StromaVasculature)+$$
$$(\sim 0.407*HIF2\alpha\_Stroma)+(\sim -1.096*CAIX\_TumorVasculature)+$$
$$(\sim 0.912*CAIX\_Tumor)+$$
$$(\sim 0.600*PDGFR\beta\_Stroma)+$$
$$(\sim 0.714*Fibronectin\_Stroma).$$

73. A kit comprising at least two labels selected from the group consisting of: a label specific for TEM1, a label specific for PDGFRβ, a label specific for HIF2α, a label specific for CAIX, a label specific for fibronectin, a label specific for collagen I, a label specific for collagen IV, and a label specific for CD31, and instructions for using the kit.
74. The kit of aspect 73 comprising a label specific for TEM1, a label specific for PDGFRβ, a label specific for HIF2α, a label specific for CAIX, and instructions for using the kit.
75. The kit of aspect 73 or aspect 74 further comprising one or more of a label specific for cell nuclei, a label specific for tumor cytoplasm, a label specific for tumor stroma, a label specific for vasculature, a label for tumor vasculature, and a label for tumor stromal vasculature.
76. The kit of aspect 75, wherein the label specific for tumor cytoplasm reacts with cytokeratin, the label specific for tumor stroma reacts with vimentin, and the label specific for vasculature reacts with CD31.
77. The kit of aspect 73 wherein said label specific for TEM1 comprises an antibody that specifically binds TEM1, said label specific for PDGFRβ comprises an antibody that specifically binds PDGFRβ, said label specific for HIF2α comprises an antibody that specifically binds HIF2α, said label specific for CAIX comprises an antibody that specifically binds CAIX, said label specific for fibronectin comprises an antibody that specifically binds fibronectin, said label specific for collagen I comprises an antibody that specifically binds collagen I, and said label specific for collagen IV comprises an antibody that specifically binds collagen IV.
78. The kit of aspect 77 wherein said antibody directed against TEM1 is produced by the hybridoma deposited with ATCC having accession number PTA-12547.
79. The kit of aspect 73 wherein each of said labels comprises a radiolabel, a fluorophore, an epitope tag, biotin, a chromophore label, an ECL label, an enzyme, ruthenium, $^{111}$In-DOTA, DAB (3, 3'-diaminobenzidine), $^{111}$In-diethylenetriaminepentaacetic acid (DTPA), horseradish peroxidase, alkaline phosphatase and beta-galactosidase, or polyhistidine.

80. The kit of aspect 79, wherein the fluorophore is selected from the group consisting of 4',6-diamidino-2-phenylindole (DAPI), fluorescein isothiocyanate (FITC), and a cyanine dye.

81. A tissue sample array comprising tumor tissue samples labeled with one or more antibodies that specifically binds to cytokeratin, vimentin, CD31, TEM1, fibronectin-1, PDGFRβ, collagen I, collagen IV, HIF2α, or CAIX, wherein each array comprises at least one tissue sample labeled with at least one antibody that specifically binds cytokeratin, vimentin, CD31, TEM1, fibronectin-1, PDGFRβ, collagen I, collagen IV, HIF2α, or CAIX.

82. The tissue sample array of aspect 80, wherein one or more of the tissue samples is labeled with a nuclear label.

83. The tissue sample array of aspect 82, wherein the nuclear label is DAPI.

84. The tissue sample array of any one of aspects 80 to 83, wherein the array comprises at least one tissue sample labeled with an antibody that specifically binds any one of cytokeratin, vimentin, or CD31, and an antibody that specifically binds any one of TEM1, fibronectin-1, PDGFRβ, collagen I, collagen IV, HIF2, or CAIX 85. The tissue sample array of any one of aspects 80 to 84 wherein the array comprises a plurality of tissue samples labeled with an antibody that specifically binds cytokeratin, where:
   at least one tissue sample labeled with an antibody that specifically binds cytokeratin further comprises an antibody that specifically binds TEM1;
   at least one tissue sample labeled with an antibody that specifically binds cytokeratin further comprises an antibody that specifically binds fibronectin-1;
   at least one tissue sample labeled with an antibody that specifically binds cytokeratin further comprises an antibody that specifically binds PDGFRβ;
   at least one tissue sample labeled with an antibody that specifically binds cytokeratin further comprises an antibody that specifically binds collagen I;
   at least one tissue sample labeled with an antibody that specifically binds cytokeratin further comprises an antibody that specifically binds collagen IV;
   at least one tissue sample labeled with an antibody that specifically binds cytokeratin further comprises an antibody that specifically binds HIF2α; and
   at least one tissue sample labeled with an antibody that specifically binds cytokeratin further comprises an antibody that specifically binds CAIX.

86. The tissue sample array of any one of aspects 80 to 84 wherein the array comprises a plurality of tissue samples labeled with an antibody that specifically binds vimentin, where:
   at least one tissue sample labeled with an antibody that specifically binds vimentin further comprises an antibody that specifically binds TEM1;
   at least one tissue sample labeled with an antibody that specifically binds vimentin further comprises an antibody that specifically binds fibronectin-1;
   at least one tissue sample labeled with an antibody that specifically binds vimentin further comprises an antibody that specifically binds PDGFRβ;
   at least one tissue sample labeled with an antibody that specifically binds vimentin further comprises an antibody that specifically binds collagen I;
   at least one tissue sample labeled with an antibody that specifically binds vimentin further comprises an antibody that specifically binds collagen IV;
   at least one tissue sample labeled with an antibody that specifically binds vimentin further comprises an antibody that specifically binds HIF2α; and
   at least one tissue sample labeled with an antibody that specifically binds vimentin further comprises an antibody that specifically binds CAIX.

87. The tissue sample array of any one of aspects 80 to 84 wherein the array comprises a plurality of tissue samples labeled with an antibody that specifically binds CD31, where:
   at least one tissue sample labeled with an antibody that specifically binds CD31 further comprises an antibody that specifically binds TEM1;
   at least one tissue sample labeled with an antibody that specifically binds CD31 further comprises an antibody that specifically binds fibronectin-1;
   at least one tissue sample labeled with an antibody that specifically binds CD31 further comprises an antibody that specifically binds PDGFRβ;
   at least one tissue sample labeled with an antibody that specifically binds CD31 further comprises an antibody that specifically binds collagen I;
   at least one tissue sample labeled with an antibody that specifically binds CD31 further comprises an antibody that specifically binds collagen IV;
   at least one tissue sample labeled with an antibody that specifically binds CD31 further comprises an antibody that specifically binds HIF2α; and
   at least one tissue sample labeled with an antibody that specifically binds CD31 further comprises an antibody that specifically binds CAIX.

88. The tissue sample array of any one of aspects 80 to 84 wherein the array comprises a plurality of tissue samples labeled with an antibody that specifically binds CD31 and an antibody that specifically binds vimentin, where:
   at least one tissue sample labeled with an antibody that specifically binds CD31 and an antibody that specifically binds vimentin further comprises an antibody that specifically binds TEM1;
   at least one tissue sample labeled with an antibody that specifically binds CD31 and an antibody that specifically binds vimentin further comprises an antibody that specifically binds fibronectin-1;
   at least one tissue sample labeled with an antibody that specifically binds CD31 and an antibody that specifically binds vimentin further comprises an antibody that specifically binds PDGFRβ;
   at least one tissue sample labeled with an antibody that specifically binds CD31 and an antibody that specifically binds vimentin further comprises an antibody that specifically binds collagen I;
   at least one tissue sample labeled with an antibody that specifically binds CD31 and an antibody that specifically binds vimentin further comprises an antibody that specifically binds collagen IV;
   at least one tissue sample labeled with an antibody that specifically binds CD31 and an antibody that specifically binds vimentin further comprises an antibody that specifically binds HIF2α and
   at least one tissue sample labeled with an antibody that specifically binds CD31 and an antibody that specifically binds vimentin further comprises an antibody that specifically binds CAIX.

89. The tissue sample array of any one of aspects 80 to 84 wherein the array comprises a plurality of tissue samples labeled with an antibody that specifically binds CD31 and an antibody that specifically binds cytokeratin, where:

at least one tissue sample labeled with an antibody that specifically binds CD31 and an antibody that specifically binds cytokeratin further comprises an antibody that specifically binds TEM1;

at least one tissue sample labeled with an antibody that specifically binds CD31 and an antibody that specifically binds cytokeratin further comprises an antibody that specifically binds fibronectin-1;

at least one tissue sample labeled with an antibody that specifically binds CD31 and an antibody that specifically binds cytokeratin further comprises an antibody that specifically binds PDGFRβ;

at least one tissue sample labeled with an antibody that specifically binds CD31 and an antibody that specifically binds cytokeratin further comprises an antibody that specifically binds collagen I;

at least one tissue sample labeled with an antibody that specifically binds CD31 and an antibody that specifically binds cytokeratin further comprises an antibody that specifically binds collagen IV;

at least one tissue sample labeled with an antibody that specifically binds CD31 and an antibody that specifically binds cytokeratin further comprises an antibody that specifically binds HIF2α; and at least one tissue sample labeled with an antibody that specifically binds CD31 and an antibody that specifically binds cytokeratin further comprises an antibody that specifically binds CAIX.

90. The tissue sample array of any one of aspects 80 to 84 wherein the array comprises a plurality of tissue samples labeled with an antibody that specifically binds cytokeratin and an antibody that specifically binds vimentin, where:

at least one tissue sample labeled with an antibody that specifically binds cytokeratin and an antibody that specifically binds vimentin further comprises an antibody that specifically binds TEM1;

at least one tissue sample labeled with an antibody that specifically binds cytokeratin and an antibody that specifically binds vimentin further comprises an antibody that specifically binds fibronectin-1;

at least one tissue sample labeled with an antibody that specifically binds cytokeratin and an antibody that specifically binds vimentin further comprises an antibody that specifically binds PDGFRβ;

at least one tissue sample labeled with an antibody that specifically binds cytokeratin and an antibody that specifically binds vimentin further comprises an antibody that specifically binds collagen I;

at least one tissue sample labeled with an antibody that specifically binds cytokeratin and an antibody that specifically binds vimentin further comprises an antibody that specifically binds collagen IV;

at least one tissue sample labeled with an antibody that specifically binds cytokeratin and an antibody that specifically binds vimentin further comprises an antibody that specifically binds HIF2α; and at least one tissue sample labeled with an antibody that specifically binds cytokeratin and an antibody that specifically binds vimentin further comprises an antibody that specifically binds CAIX.

91. The tissue sample array of aspect 80, wherein the array comprises a plurality of tissue samples, any one or more of which are labeled with any one of the labeling combinations of aspects 85 to 90.

92. The tissue sample array of aspect 80, wherein the array comprises:

at least one tissue sample labeled with an antibody specific for vimentin and is also labeled with one antibody specific for TEM1;

at least one tissue sample labeled with an antibody specific for cytokeratin, an antibody specific for CD31, and is also labeled with one antibody specific for TEM1;

at least one tissue sample labeled with an antibody specific for vimentin, an antibody specific for CD31, and is also labeled with one antibody specific for HIF2α;

at least one tissue sample labeled with an antibody specific for vimentin, and is also labeled with one antibody specific for HIF2α;

at least one tissue sample labeled with an antibody specific for cytokeratin and is also labeled with one antibody specific for CAIX;

at least one tissue sample labeled with an antibody specific for cytokeratin, an antibody specific for CD31, and is also labeled with one antibody specific for CAIX;

at least one tissue sample labeled with an antibody specific for vimentin, an antibody specific for CD31, and is also labeled with one antibody specific for PDGFRβ; and at least one tissue sample labeled with an antibody specific for vimentin and is also labeled with one antibody specific for fibronectin-1.

93. The tissue sample array of aspect 80, wherein the array comprises a plurality of tissue samples labeled with one or more of:

an antibody that specifically binds TEM1,
an antibody that specifically binds HIF2α,
an antibody that specifically binds CAIX, and
an antibody that specifically binds PDGFRβ.

94. The tissue sample array of aspect 93, wherein the array comprises a plurality of tissue samples, wherein:

at least one tissue sample in the array is labeled with an antibody that specifically binds TEM1,
at least one tissue sample in the array is labeled with an antibody that specifically binds HIF2α,
at least one tissue sample in the array is labeled with an antibody that specifically binds CAIX, and
at least one tissue sample in the array is labeled with an antibody that specifically binds PDGFRβ.

95. The tissue sample array of aspect 94, wherein the tissue samples labeled with an antibody that specifically binds TEM1, HIF2α, CAIX, or PDGFRβ, further comprises any one or more of:

an antibody that specifically binds vimentin,
an antibody that specifically binds cytokeratin, or
an antibody that specifically binds CD31.

96. The tissue sample array of aspect 93 or 94, wherein at least one tissue sample in the array is labeled with a combination of any two of the recited antibodies.

97. The tissue sample array of aspect 93 or 94, wherein at least one tissue sample in the array is labeled with a combination of any three of the recited antibodies.

98. The tissue sample array of aspect 93 or 94, wherein at least one tissue sample in the array is labeled with a combination of any four of the recited antibodies.

99. The tissue sample array of aspect 93 or 94, wherein at least one tissue sample in the array is labeled with a combination of any five of the recited antibodies.

100. The tissue sample array of aspect 93 or 94, wherein at least one tissue sample in the array is labeled with a combination of any six of the recited antibodies.

101. The tissue sample array of aspect 93 or 94, wherein at least one tissue sample in the array is labeled with all seven of the recited antibodies.

102. The tissue sample array of aspect 80, wherein the array comprises a plurality of tissue samples, wherein the array is labeled with any three of the following:
an antibody that specifically binds TEM1,
an antibody that specifically binds HIF2α,
an antibody that specifically binds CAIX, and
an antibody that specifically binds PDGFRβ.

103. The tissue sample array of aspect 102, wherein the array further comprises any one or more of:
an antibody that specifically binds vimentin,
an antibody that specifically binds cytokeratin, or
an antibody that specifically binds CD31.

104. The tissue sample array of aspect 80, wherein the array comprises a plurality of tissue samples, wherein the array is labeled with any two of the following:
an antibody that specifically binds TEM1,
an antibody that specifically binds HIF2α,
an antibody that specifically binds CAIX, and
an antibody that specifically binds PDGFRβ.

105. The tissue sample array of aspect 104, wherein the array further comprises any one or more of:
an antibody that specifically binds vimentin,
an antibody that specifically binds cytokeratin, or
an antibody that specifically binds CD31.

106. The tissue sample array of any one of aspects 103 to 105, further comprising one or more of:
an antibody that specifically binds fibronectin-1,
an antibody that specifically binds collagen I, and
an antibody that specifically binds collagen IV.

107. The tissue sample array of any one of aspects 80 to 106, wherein the tumor tissue samples of the array are obtained from the same tumor.

108. The tissue sample array of any one of aspects 80 to 106, wherein the tumor tissue samples of the array are obtained from different tumors.

109. The tissue sample array of aspect 107 or 108, wherein the tumor tissue samples are histological sections.

110. The tissue sample array of aspect 109, wherein the tumor tissue samples are histological sections obtained from a subject having colorectal cancer.

Having described the invention, the same will be more readily understood through reference to the following Examples, which are provided by way of illustration, and are not intended to limit the invention in any way.

EXAMPLES

Example 1: Primary Localization of Biomarker Panel

Cellular localization and expression profiles of putative TEM-1 associated biomarkers, were assessed using histological samples. The histological samples for these studies were obtained from the Yale Colorectal Cancer Cohort (YTMA8), which consisted of tumor microarrays (TMAs) constructed at the Yale University Tissue Microarray Facility (New Haven, Conn.). The TMAs contained 599 primary colorectal carcinomas (CRCs) from formalin fixed, paraffin-embedded tumor samples obtained at Yale University-New Haven Hospital (New Haven, Conn.) from 1970-1981. Each tumor sample block was sectioned and first stained by hematoxylin and eosin (H&E) so that areas of invasive tumor could be identified and circled. The circled region was then transcribed onto the original block from which 0.6 mm cores were taken. Each core was arrayed into recipient blocks in a 1 mm-spaced grid, and 5-micron thick sections were prepared. Clinicopathological variables available for this cohort include T-stage, N-Stage, histological grade, organ site, gender, and age. Univariate Cox Proportional Hazard modeling based on five-year disease-specific survival for each clinicopathological variable for both the entire cohort (all available clinical information) as well as for only the cases with complete data used in the multivariate analysis in this study can be found in Table 1.

Each putative TEM-1-associated biomarker (TEM-1, HIF2α, CAIX, PDGFRβ, fibronectin (FN), collagen I (COLI), and collagen IV (COLIV)) was quantified in all cellular and sub-cellular compartments of interest using quantitative immunohistochemistry (IHC) analysis (AQUA® technology, HistoRx, Inc.). Each TEM-1 associated biomarker was analyzed in the presence of DAPI (4',6-diamidino-2-phenylindole) to identify nuclei, fluorescently labeled cytokeratin to identify tumor cytoplasm, fluorescently labeled vimentin to identify stroma, and fluorescently labeled CD-31 to identify vasculature. The labeled histological samples were then analyzed using advanced image analysis algorithms to generate a binary image identifying each pixel as either included or excluded from each histological compartment of interest FIG. 1A provides examples of each target and respective compartments used in this study. FIG. 1B provides an example of the label localization seen with each of the potential biomarkers tested. The quantity of each biomarker of interest was determined for each histological compartment of interest and these values were translated into AQUA® scores for each biomarker. Four histological compartments of interest were assessed: tumor (membrane/cytoplasm), tumor vasculature, pure stroma (stroma without contributing vasculature), and stromal vasculature. The mean and 95% confidence interval for AQUA® scores for each compartment were plotted to determine the histological compartment(s) with the highest expression. Based on these data and for subsequent statistical analyses, AQUA® scores from all compartments were included for TEM-1, stroma and stromal vasculature for HIF2α, tumor and tumor vasculature for CAIX, stroma and stromal vasculature for PDGFRβ, stroma for FN, stroma and stromal vasculature for COLI, and stroma and stromal vasculature for COLIV.

Immunohistochemistry (IHC)

Immunofluorescence staining for AQUA® analyses has been described in U.S. Pat. No. 7,219,016, and in U.S. Patent Application Publication No. 2009/0034823, each of which is incorporated by reference into this application in its entirety. In brief, pre-cut paraffin-coated tissue microarray slides were de-paraffinized and antigen-retrieval for slides to be stained for TEM-1 and CAIX was done using a Decloaking Chamber with a 10× DIVA buffer, pH 6.2 (Biocare Medical DV2004MX). Slides were incubated for 15 minutes inside the chamber where pressurized incubation reached a maximum of 125° C. at 15-20 PSI for 30 seconds followed by cool down for 15 minutes down to 95° C. Antigen retrieval for slides to be stained for PDGFRβ, Fibronectin, HIF2α, Collagen I and Collagen IV was done in PT Module (Labvision, Fremont, Calif.) with Tris EDTA buffer, pH9. Staining was performed on a LabVision Autostainer (Labvision, Fremont, Calif.) according to previously described protocols. Slides were incubated for one hour at room temperature with mouse anti-CD-31 (DAKO, clone JC70A, lot#00079267) for TEM-1, CAIX, Fibronectin, PDGFRβ, Collagen I, Collagen IV, or rabbit anti-CD-31 (Abcam, lot# GR-61759-4) for HIF2α. Following CD-31 antibody incubation, slides were rinsed in 1×TBS-Tween and then incubated with mouse Envision™ Plus (DAKO, Carpinteria, Calif.) or rabbit Envision™ Plus (DAKO, Carpinteria, Calif.) for 30 minutes at room temperature. Slides were then rinsed with 1×TBS-Tween and incubated with biotinylated tyramide (TSA plus Biotin system, Perkin Elmer) for 10 minutes at room temperature. Slides were rinsed with 1×TBS-Tween® and this was followed by two incubations of benzoic hydrazide (Sigma Aldrich) and hydrogen peroxide for 8 min at first and second for 7 minute. Slides were rinsed with 1×TBS-Tween® and incubated with Alexa Fluor® 750 streptavidin. This was followed by incubation with the primary antibody TEM-1 rat (Morphotek, clone 9G5, lot#26089C) or Fibronectin-1 rabbit (Abcam, lot #GR16465-1) or PDGFRβ rabbit (Cell Signaling, clone 28E1, lot #3169S) or Collagen I rabbit (Fitzgerald, lot #70R-CR007x) or Collagen IV rabbit (Fitzgerald, lot #70R-CR013x) or HIF2α mouse (Novus Biologicals, clone ep190b, lot # J-3) or CAIX rat (Morphotek, clone 165F3) for one hour at room temperature. Primary antibody was included in a cocktail with chicken anti-vimentin (Millipore, lot #2028291, 1:200). Following primary antibody incubation, slides were rinsed in 1×TBS-Tween and then incubated with secondary antibody Immpress anti-rat (Vector laboratories, TEM-1 and CAIX) or Impress anti-rabbit (Vector Laboratories, Fibronectin, PDGFRβ, Collagen I, Collagen IV) or ImmPRESS™ anti-mouse (Vector Laboratories, HIF2α) for thirty minutes at room temperature. Slides were then incubated with a cocktail of Alexa Fluor® 555 conjugated anti-chicken (Invitrogen, A21437, Carlsbad, Calif., 1:200) for half hour at room temperature. Following Alexa Fluor) staining slides were incubated with mouse IgG block (Biocare Medical, NC494 H) and then with Alexa Fluor@ 488 Pan Cytokeratin, clone AE1/AE3 (eBioscience, 53-9003-82) for 30 minutes at room temperature. Slides were then incubated with the Cy5 tyramide amplification system (Perkin Elmer, SAT705A, 1:50 dilution in amplification buffer, Waltham, Mass.) for 10 minutes, mounted with Prolong anti-fade with DAPI (Invitrogen, P36931, Carlsbad, Calif.) for the identification of nuclei within each histospot, and allowed to dry overnight.

Imaging and Image Analysis

Relative protein concentration within subcellular compartments can be measured with a high degree of precision using the AQUA® analysis system. In brief, high resolution, 12 bit (resulting in 4096 discrete intensity values per pixel of an acquired image) digital images of the cytokeratin with FITC, vimentin with Cy3, nuclear staining with DAPI, biomarker panel staining with Cy5 and CD-31 with Cy7 were captured and saved for every histospot on the array using the PM2000 epi-fluorescence microscopy system (HistoRx, Inc., New Haven, Conn.). Prior to statistical analysis, images were reviewed for quality (e.g. poor tissue, saturation, focus and other artifacts) and signal intensity of the DAPI and Cy3 signals. The pan-cytokeratin signal was used to create an epithelial "mask" to distinguish regions of epithelial tissue from stromal elements within both the normal and tumor samples. Vimentin was used to create a total stroma specific mask. CD-31 was used to create a vasculature specific mask. Using the combination of these masks tumor vasculature stromal vasculature and pure stroma (Total Stroma excluding Stroma vasculatures) compartments were generated.

TABLE 1

Univariate Cox-Proportional Hazards modeling for clinicopathological characteristics for YTMA8.

| | All Cases (N = 604) | | | | | Cases Included in Multivariate Analysis (N = 170) | | | | |
|---|---|---|---|---|---|---|---|---|---|---|
| Parameter | No. | %* | Hazard Ratio | 95% CI | p-value^ | Parameter | No. | %* | Hazard Ratio | 95% CI | p-value^ |
| T-Stage | | | | | | T-Stage | | | | | |
| T1 | 20 | 3.7 | 1.00 | | | T1 | 3 | 1.8 | 1.00 | | |
| T2 | 187 | 34.9 | 1.18 | 0.42-3.28 | 0.750 | T2 | 53 | 31.2 | 0.30 | 0.07-1.33 | 0.112 |
| T3 | 326 | 60.8 | 2.75 | 1.02-7.44 | 0.050 | T3 | 113 | 66.5 | 0.71 | 0.17-2.90 | 0.630 |
| T4 | 3 | 0.6 | 22.23 | 4.91-100.7 | <0.001 | T4 | 1 | 0.6 | 19.46 | 1.53-247.7 | 0.022 |
| N-Stage | | | | | | N-Stage | | | | | |
| N0 | 286 | 54.6 | 1.00 | | | N0 | 89 | 52.4 | 1.00 | | |
| N1 | 159 | 30.3 | 2.36 | 1.70-3.27 | <0.001 | N1 | 47 | 27.6 | 2.30 | 1.31-4.03 | 0.004 |
| N2 | 79 | 15.1 | 4.27 | 2.96-6.15 | <0.001 | N2 | 34 | 20.0 | 3.24 | 1.80-5.83 | <0.001 |
| Histological Grade | | | | | | Histological Grade | | | | | |
| Well Differentiated | 193 | 39.6 | 1.00 | | | Well Differentiated | 64 | 37.6 | 1.00 | | |
| Moderate Differentiated | 231 | 47.4 | 1.35 | 0.99-1.86 | 0.060 | Moderate Differentiated | 80 | 47.1 | 1.56 | 0.92-2.66 | 0.102 |
| Poorly Differentiated | 63 | 12.9 | 1.85 | 1.20-2.83 | 0.005 | Poorly Differentiated | 26 | 15.3 | 1.88 | 0.95-3.74 | 0.071 |
| Organ Site | | | | | | Organ Site | | | | | |
| Colon | 456 | 75.5 | 1.00 | | | Colon | 118 | 69.4 | 1.00 | | |
| Rectum | 148 | 24.5 | 0.97 | 0.72-1.32 | 0.860 | Rectum | 52 | 30.6 | 0.85 | 0.50-1.44 | 0.541 |
| Gender | | | | | | Gender | | | | | |
| Female | 334 | 55.3 | 1.00 | | | Female | 94 | 55.3 | 1.00 | | |
| Male | 270 | 44.7 | 1.28 | 0.99-1.66 | 0.060 | Male | 76 | 44.7 | 2.02 | 1.26-3.25 | 0.004 |
| Age (continuous) | 604 | 100 | 1.01 | 0.99-1.02 | 0.310 | Age (continuous) | 170 | 100 | 1.01 | 0.98-1.03 | 0.604 |

Median disease-specific survival = 192.4 months (Range of Follow-up time: 0.43-380.4 months)
*Represents % of cases with clinical information
^Cox univariate analysis (5-year disease-specific survival)

Statistical Analysis

Unsupervised hierarchical clustering was performed using the Multiple Experiment Viewer of the TM4 Microarray Software Suite (Saeed et al., Biotechniques 34(2):374-8 (2003)). Clustering was performed using average linkage clustering by Person's uncentered correlation. All analyses were conducted using SPSS v17 or later (SPSS Inc., Chicago, Ill.). AQUA® scores for all biomarkers showed a skewed distribution and therefore the log base 2 transformed scores were used for subsequent parametric analyses (i.e. means comparisons). However, to provide linear comparisons, raw AQUA® score data is sometimes reported. Differences in mean scores between clinical features were assessed by general linear modeling based on one-way ANOVA. Optimal cut-point and Kaplan-Meier analysis for biomarkers with respect to 5-year disease specific survival was performed using X-Tile™ (Camp REF) correcting for multiple comparisons using Monte-Carlo simulations. For X-Tile™ analysis, two p-values are reported, the uncorrected p-value and the corrected by Montel Carlo simulations P-value. Although the uncorrected p-value may be significant (<0.05), the corrected P-value may not be significant indicating the need for further validation of the finding. Cox proportional hazards modeling was performed in the multivariate setting using backwards elimination by Wald Statistics for determining the optimal analytical model. Log-likelihood chi-squared ratios (LR-$\chi$2) were used to compare models. All survival analysis was based on five-year disease-specific survival. Kaplan-Meier survival was compared using log-rank statistics.

Example 2: Association with Clinicopathological Variables

Analyses were conducted to determine the associations for AQUA® scores in primary localization compartments of each biomarker with the available clinicopathological variables T-stage, N-stage, histologic grade, sex, tumor site and age (data not shown). In summary, the findings indicated stromal TEM-1 had significantly increased expression in well differentiated tumors; CAIX tumor vasculature expression was significantly higher in younger patients; PDGFR$\beta$ expression in both stroma and stroma vasculature was significantly higher in males; FN expression was significantly higher in node positive cases; HIF2$\alpha$ stromal expression was significantly higher in poorly differentiated tumors while HIF2$\alpha$ stromal vasculature expression was significantly higher in node negative cases; and Collagen I stromal vasculature expression was significantly higher in node positive cases.

Example 3: Univariate Survival Analysis

Tumor-associated expression and quantitation of each of the assessed biomarkers was analyzed in view of clinical outcomes for the samples assessed. Optimal Kaplan-Meier survival cutpoints were defined within continuous AQUA® score data using X-Tile for optimal cut-point analysis. Five-year disease-free survival data associated with TEM-1 expression is summarized in Table 2.

TABLE 2

| Compartment | Cut-point (AQUA ® score) | % Pop. High | Uncorrected p-value | Corrected p-value | Direction of High Expression |
|---|---|---|---|---|---|
| Tumor | 276.11 | 83.2% | 0.0009 | 0.025 | Increased survival |
| Tumor Vessel | 468.38 | 57.4% | 0.04 | 0.4 | Increased survival |
| Stromal Vessel | 613.2 | 53.2% | 0.006 | 0.08 | Increased survival |
| Pure Stroma | 473.58 | 65.0% | 0.0001 | 0.009 | Increased survival |

Results of these analyses showed that TEM-1, especially stromal expression, significantly associates with better (increased) five-year disease-specific survival in CRC. CAIX tumor vessel expression significantly associates with better (increased) five-year disease-specific survival, while stromal FN, collagen I, and collagen IV expression significantly associates with worse (decreased) five-year disease-specific survival. No significant association with survival was observed for PDGFR$\beta$ or HIF2$\alpha$.

Example 4: Generation of TAPPS Score Model and Prognostic Value

Expression profiles of selected biomarkers (TEM1 in stroma, TEM1 in tumor, TEM1 in stroma vessel, TEM1 in tumor vessel, HIF2$\alpha$ in stroma vessel, HIF2$\alpha$ in stroma, CAIX in tumor vessel, CAIX in tumor, PDGFR$\beta$ in stroma vessel, PDGFR$\beta$ in stroma, fibronectin in stroma, collagen I in stroma vessel, collagen I in stroma, collagen IV in stroma vessel, and collagen IV in stroma) were examined together in a multivariate Cox Proportional Hazards model using the univariate cut-points. In total, these 15 binarized variables (low expression versus high expression) were entered into a Cox Proportional Hazards model using backwards elimination with a set to 0.10 based on Wald statistics to provide the optimal prognostic model. The results are shown in Table 3, where p=$3.92\times10^{-10}$ for the optimal model and optimal AQUA® score cut-points for each marker/biological compartment included in the model are shown.

TABLE 3

Optimal prognostic TAPPS score model in colorectal cancer.

| Marker | AQUA ® Score Cut-point | Hazard Ratio | 95% CI | p-value | Coefficient |
|---|---|---|---|---|---|
| TEM1 Stroma | 473.58 | 0.35 | 0.19-0.62 | <0.001 | −1.06 |
| TEM1 Tumor Vasculature | 468.38 | 1.61 | 0.92-2.82 | 0.093 | 0.48 |
| HIF2α Stroma Vasculature | 1857.51 | 0.34 | 0.19-0.59 | <0.001 | −1.10 |
| HIF2α Stroma | 2005.59 | 1.50 | 0.95-2.37 | 0.081 | 0.41 |
| CAIX Tumor Vasculature | 3290.39 | 0.33 | 0.17-0.67 | 0.002 | −1.10 |
| CAIX Tumor | 595.67 | 2.49 | 0.99-6.20 | 0.050 | 0.91 |
| PDGFRβ Stroma | 6272.84 | 1.82 | 1.06-3.14 | 0.031 | 0.60 |
| Fibronectin Stroma | 9883.19 | 2.04 | 1.21-3.44 | 0.007 | 0.71 |

From this model, a coefficient was derived for each marker, and as such, with these coefficients an equation was developed that provides an overall risk score, termed TAPPS for TEM-1 Associated Pathway Prognostic Signature.
The TAPPS score equation for this cohort is as follows:

(−1.063*TEM1_Stroma)+
(0.478*TEM1_TumorVasculature)+(−1.095*HIF2α_StromaVasculature)+
(0.407*HIF2α_Stroma)+(−1.096*CAIX_TumorVasculature)+
(0.912*CAIX_Tumor)+
(0.600*PDGFRβ_Stroma)+
(0.714*Fibronectin_Stroma).

Figure 2A:
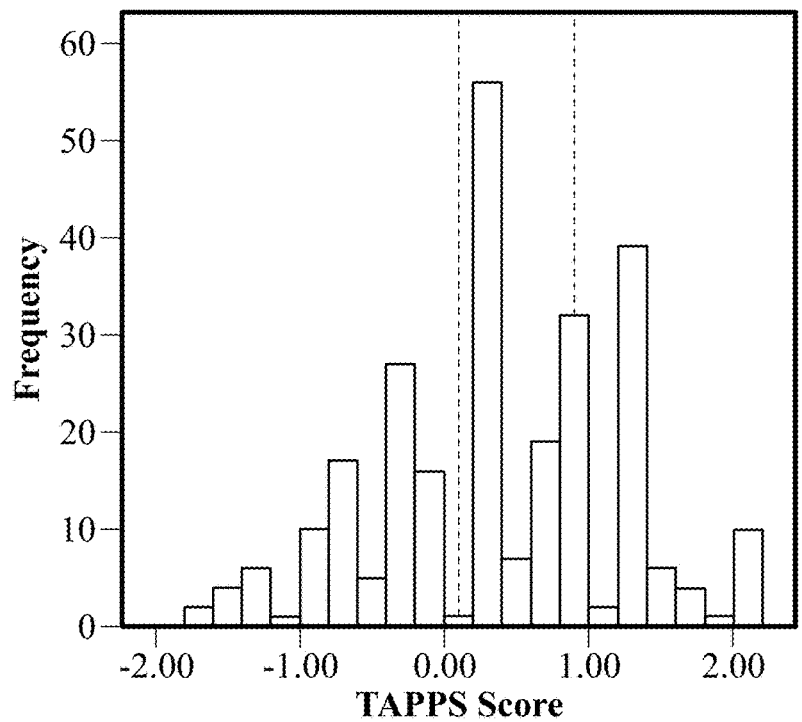
FIG. 2 shows that the TAPPS score is highly prognostic in colorectal cancer. (A) Histogram plot of the TAPPS score distribution on YTMA8 (n=265). Dotted lines represent the tertile cut-points used for survival analysis. (B) Kaplan-Meier survival analysis of all cases with 5-year disease-free survival. Low TAPPS (dark gray line on top at time 60 months) n=88, events=15, Intermediate TAPPS (light gray line in middle at time 60 months) n=99, events=38, High TAPPS (black line on bottom at time 60 months) n=73, events=51. (C) Kaplan-Meier survival analysis of node negative cases only with 5-year disease-free survival. Low TAPPS (dark gray line on top at time 60 months) n=44, events=4, Intermediate TAPPS (light gray line in middle at time 60 months) n=50, events=9, High TAPPS (black line on bottom at time 60 months) n=26, events=15. (D) Kaplan-Meier survival analysis of node positive cases only with 5-year disease-free survival. Low TAPPS (light gray line in middle at time 60 months) n=27, events=6, Intermediate TAPPS (dark gray line on top at time 60 months) n=37, events=24, High TAPPS (black line on bottom at time 60 months) n=41, events=32.
Figure 2B:
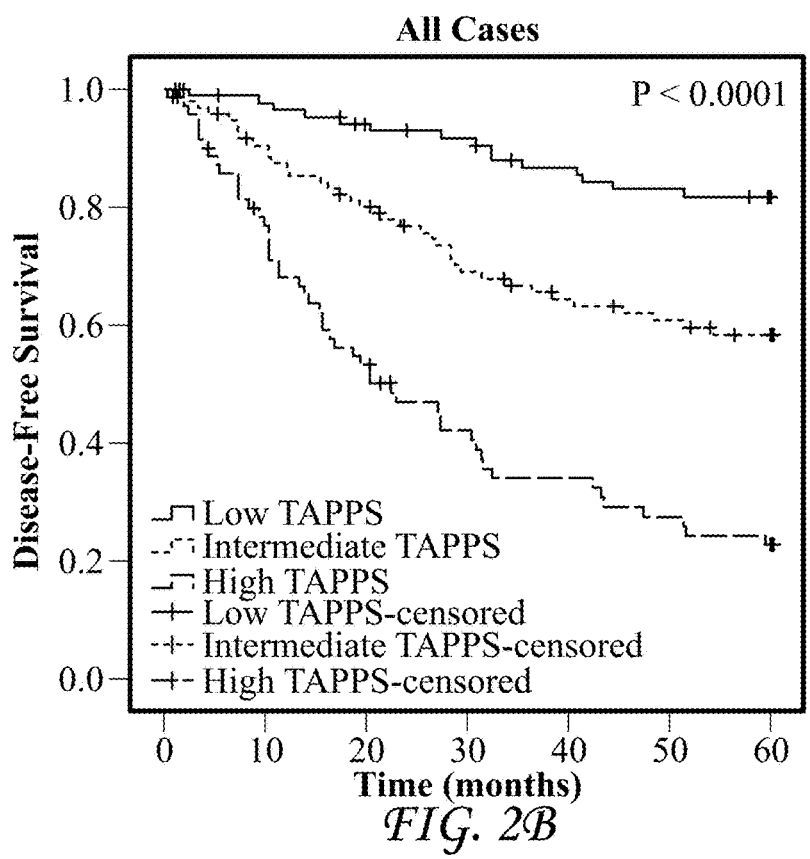
Figure 2C:
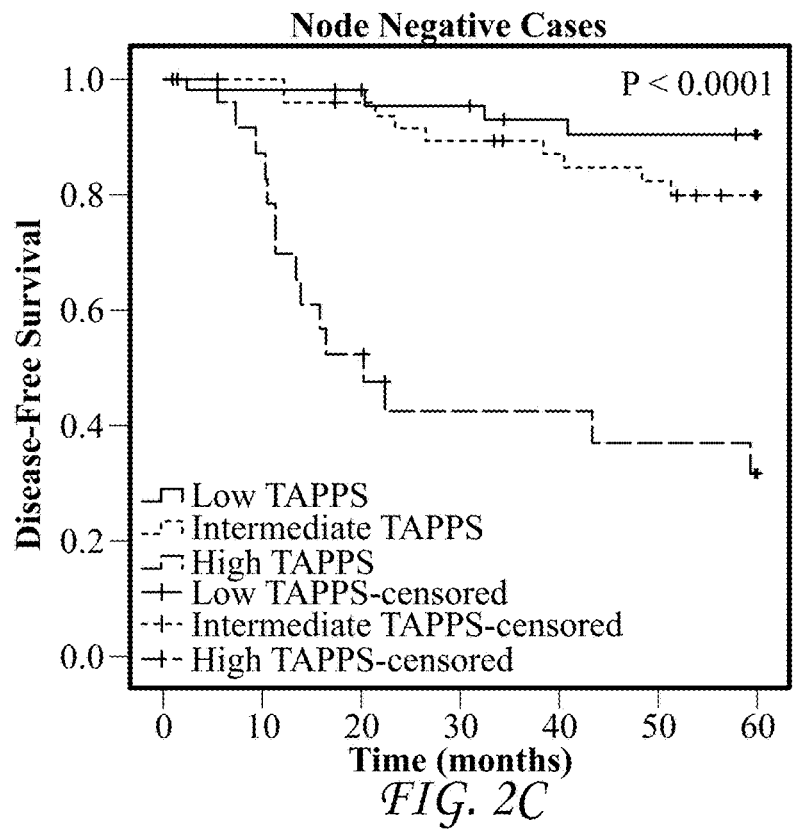
Figure 2D:
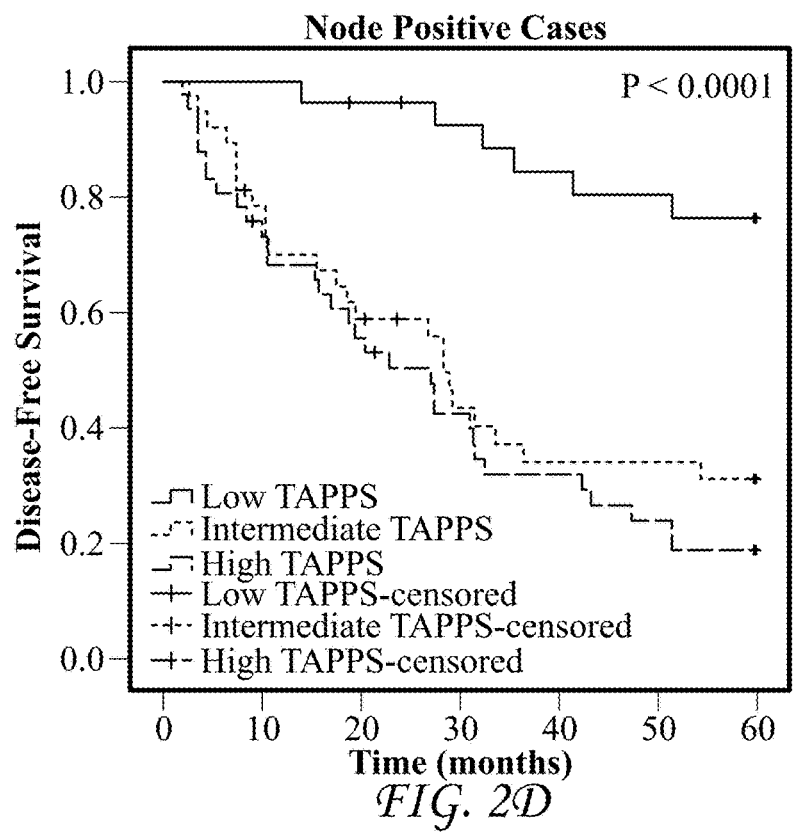

As a proof of concept, TAPPS scores for each patient in this CRC cohort were generated. The distribution of TAPPS scores FIG. 2A, which shows a near-normal distribution of TAPPS scores. The patient population was then divided into tertiles (FIG. 2A). The TAPPS score ranges from −1.75 to 2.10. The low risk group TAPPS score range is −1.75-0.00; intermediate TAPPS score range is 0.00-0.91, and high TAPPS score range is 0.91-2.10. Kaplan-Meier survival analysis showed, as expected, that patients with high TAPPS scores have a significantly decreased 5-year survival as compared to patients with intermediate TAPPS scores and patients with intermediate TAPPS scores have a significantly decreased prognosis when compared to patients with low TAPPS scores (p<0.0001, FIG. 2B). Interestingly, when using the same tertile TAPPS score cut-points in only the node negative patients, it was found that high TAPPS score could distinguish a subset of node negative patients with significantly decreased prognosis when compared to either the intermediate or low TAPPS score populations (p<0.0001, FIG. 2C). Additionally, the same analysis in only the node positive patients indicated that patients with a low TAPPS score had significantly increased survival when compared to patients with either intermediate or high TAPPS scores (p<0.0001, FIG. 2D). As shown in Table 4, Cox Proportional Hazards modeling was used to determine the independent prognostic value of TAPPS score as a continuous variable either in all cases with complete data (left) or node negative patients only (right). The continuous TAPPS score was independent and significant in a Cox Proportional Hazards multivariate model adjusted for nodal status (N-Stage), T-stage and histological grade in all patients (hazard ratio 2.7, p<0.001) and independent of T-stage and histological grade in the node negative patients only (hazard ratio 3.7, p<0.001).

TABLE 4

Multivariate analysis of TAPPS score with clinicopathological variables.

| | All Patients (N = 170) | | Node Negative Patients (N = 89) | |
|---|---|---|---|---|
| Characteristic | Hazard Ratio (95% CI) | p-value | Hazard Ratio (95% CI) | p-value |
| T-Stage | | | | |
| T1 | 1.00 | | 1 | |
| T2 | 0.250 (0.06-1.14) | 0.074 | 0.196 (0.02-1.82) | 0.152 |
| T3 | 0.500 (0.12-2.12) | 0.347 | 0.33 (0.04-2.92) | 0.318 |
| T4 | 4.519 (0.32-64.22) | 0.265 | N/A | |
| N-Stage | | | | |
| N0 | 1.00 | | N/A | |
| N1 | 1.667 (0.93-2.98) | 0.085 | N/A | |
| N2 | 1.898 (1.03-3.49) | 0.039 | N/A | |
| Histologic Grade | | | | |
| Well Diff | 1.00 | | 1 | |
| Mod Diff | 1.217 (0.70-2.13) | 0.492 | 1.021 (0.43-2.42) | 0.963 |
| Poor Diff | 1.579 (0.78-3.20) | 0.206 | 0.483 (0.10-2.32) | 0.363 |
| TAPPS Score (continuous) | 2.665 (1.92-3.69) | <0.0001 | 3.706 | <0.0001 |

An additional model was generated in which expression profiles of the same set of selected biomarkers (TEM1 in stroma, TEM1 in tumor, TEM1 in stroma vessel, TEM1 in tumor vessel, HIF2α in stroma vessel, HIF2α in stroma, CAIX in tumor vessel, CAIX in tumor, PDGFRβ in stroma vessel, PDGFRβ in stroma, fibronectin in stroma, collagen I in stroma vessel, collagen I in stroma, collagen IV in stroma vessel, and collagen IV in stroma) were examined together in a multivariate Cox Proportional Hazards model using the univariate cut-points. In total, these 15 binarized variables (low expression versus high expression) were entered into a Cox Proportional Hazards model using backwards elimination with α set to 0.10 based on Wald statistics to provide an additional prognostic model. The results are shown in Table 5.

TABLE 5

| | B | SE | Wald | df | Sig. | Exp (B) | 95% CI for Exp (B) Lower | Upper |
|---|---|---|---|---|---|---|---|---|
| TEM1 Stroma | −0.796 | 0.248 | 10.287 | 1 | 0.001 | 0.451 | 0.278 | 0.734 |
| TEM1 Tumor Vessel | 0.312 | 0.249 | 1.567 | 1 | 0.211 | 1.366 | 0.838 | 2.227 |
| CAIX Tumor | 0.905 | 0.368 | 6.066 | 1 | 0.014 | 2.472 | 1.203 | 5.081 |
| CAIX Tumor Vessel | −1.071 | 0.309 | 12.031 | 1 | 0.001 | 0.343 | 0.187 | 0.628 |

From this model, a coefficient was derived for each marker, and as such, with these coefficients an alternate TAPPS equation was developed.

The alternate TAPPS equation for this cohort is as follows:

(−0.796*TEM1_Stroma)+
(0.312*TEM1_TumorVasculature)+(−
1.071*CAIX_TumorVasculature)+(0.905*CAIX_Tumor).

Example 5: Total Expression Analysis

TMAs containing originally a total of 599 primary colorectal carcinomas (CRCs) from formalin fixed, paraffin-embedded tumor samples obtained at Yale University-New Haven Hospital (New Haven, Conn.) from 1970-1981 were constructed at the Yale University Tissue Microarray Facility (New Haven, Conn.) as described in detail elsewhere (REFS: Rimm TMA reviews). Of 599 cases, 494 had both biomarker data and clinical data. The cohort was split into training (67%) and validation (33%) sets based on sequential enrollment from diagnosis date (2 cases to the training set, and 1 case to the validation set).

Clinical variables available for this cohort include Duke's Staging, histological grade, sex, and age. Chi-square analysis showed no significant differences in proportion of clinical variables between training and validation sets (Table 6). Median disease-specific follow-up was 24 months with a median age of 68 years. Cox proportional hazard modeling based on five-year disease-specific survival for each clinical variable show expected decreases in survival for advanced stage and males, but no significant differences are observed for histological grade and age (Table 6).

Figure 3:
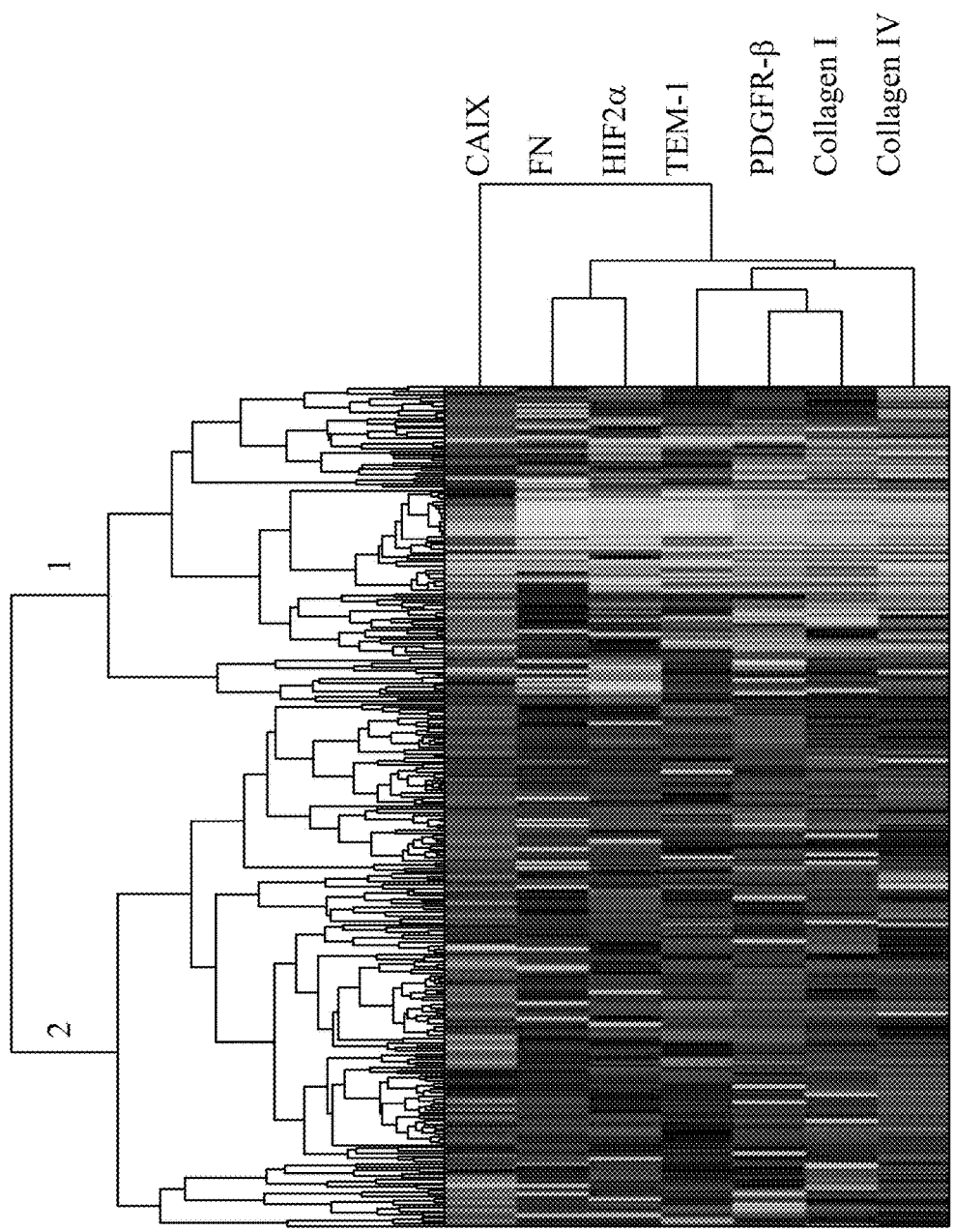
FIG. 3 shows a schematic representation of two main patient clusters identified by unsupervised hierarchical clustering of the noted biomarkers.
Figure 4A:
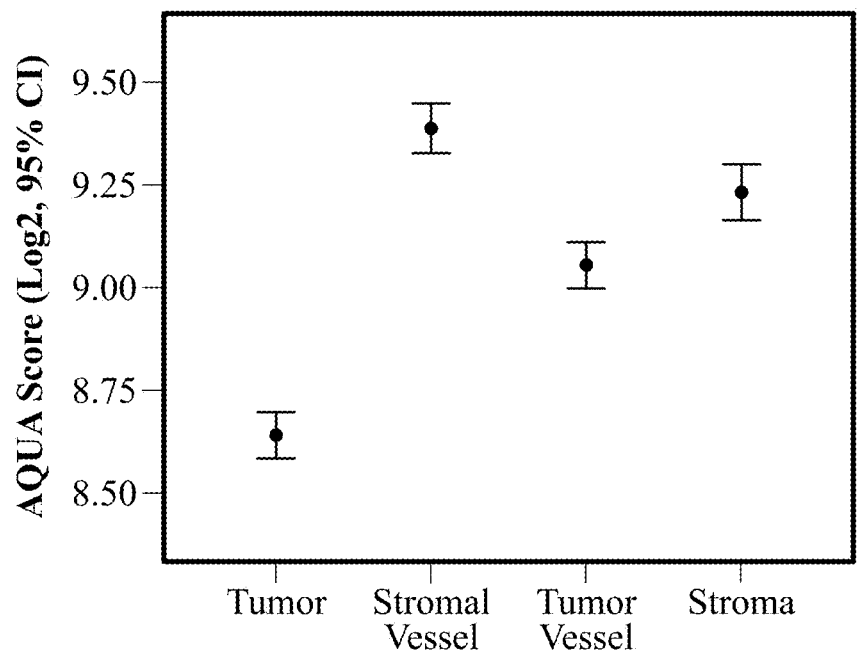
FIG. 4A shows expression of TEM-1.
Figure 4B:
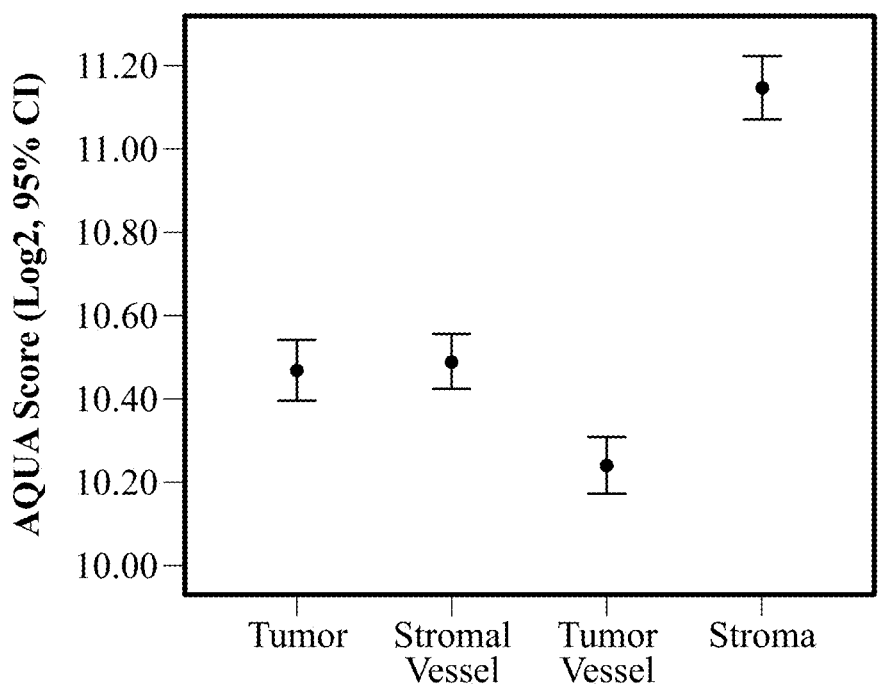
FIG. 4B shows expression of HIF2α.
Figure 4C:
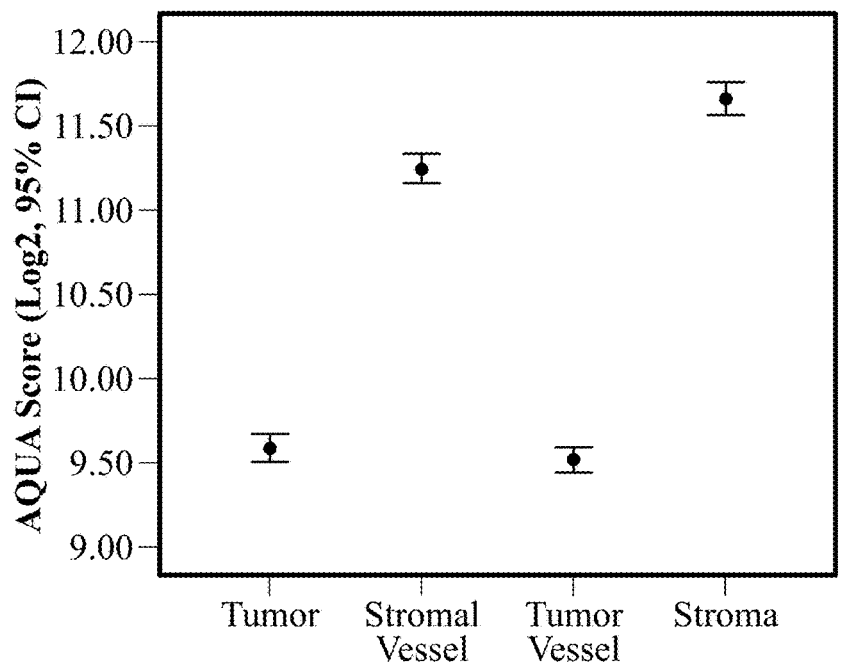
FIG. 4C shows expression of PDGFR-β.
Figure 4D:
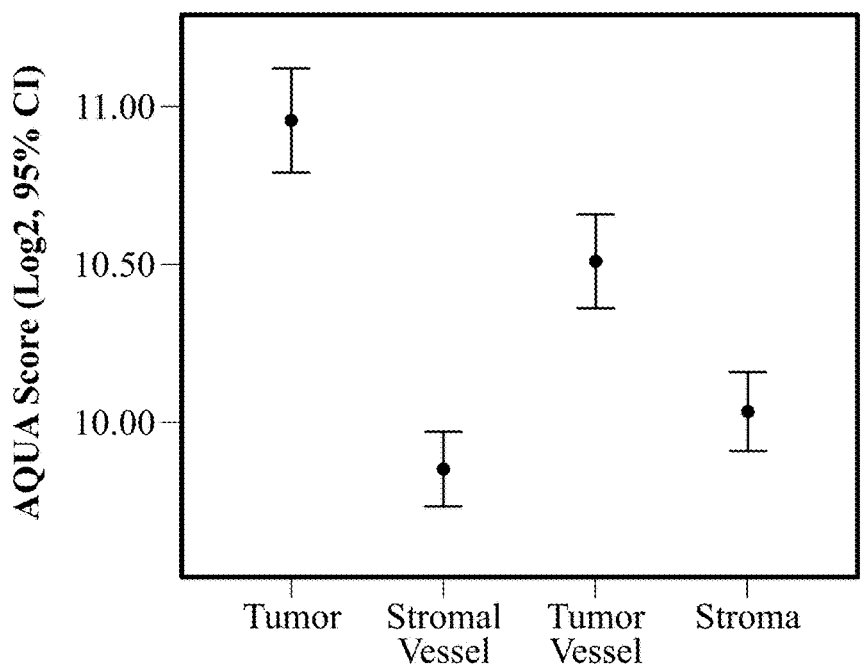
FIG. 4D shows expression of CAIX.
Figure 4E:
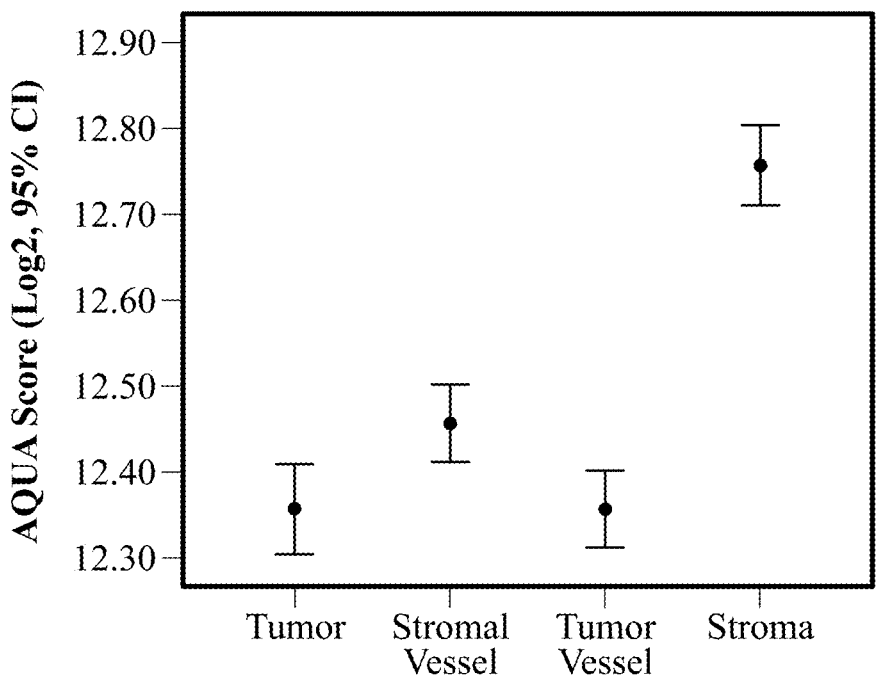
FIG. 4E shows expression of fibronectin.
Figure 4F:
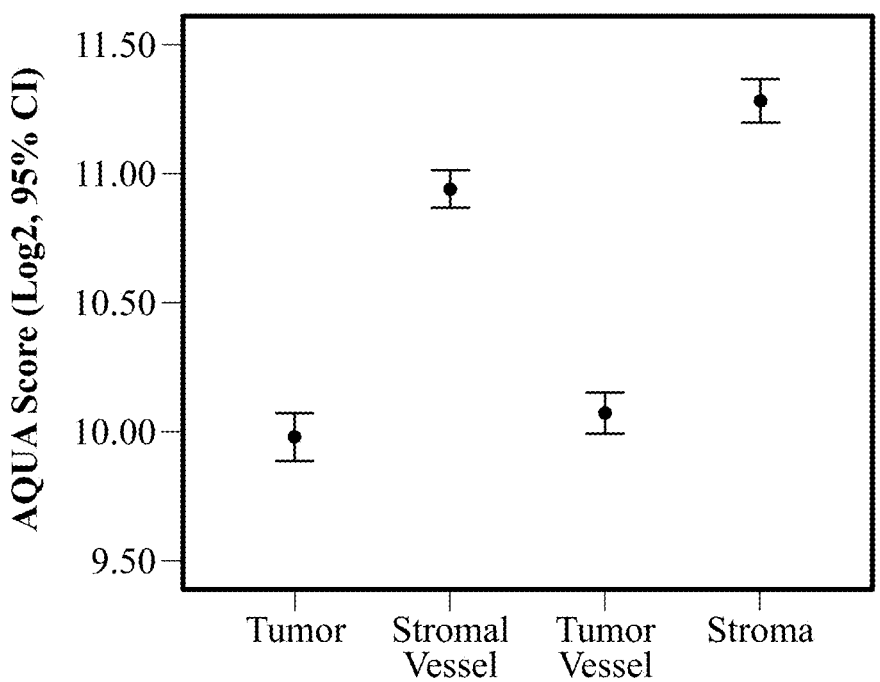
FIG. 4F shows expression of collagen I.
Figure 4G:
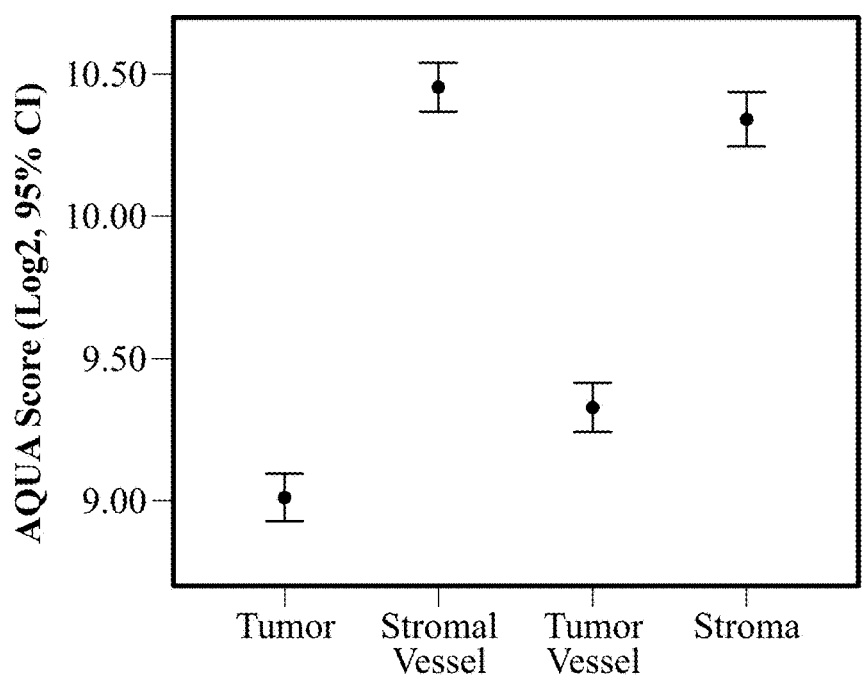
FIG. 4G shows expression of collagen IV.
Figure 5A:
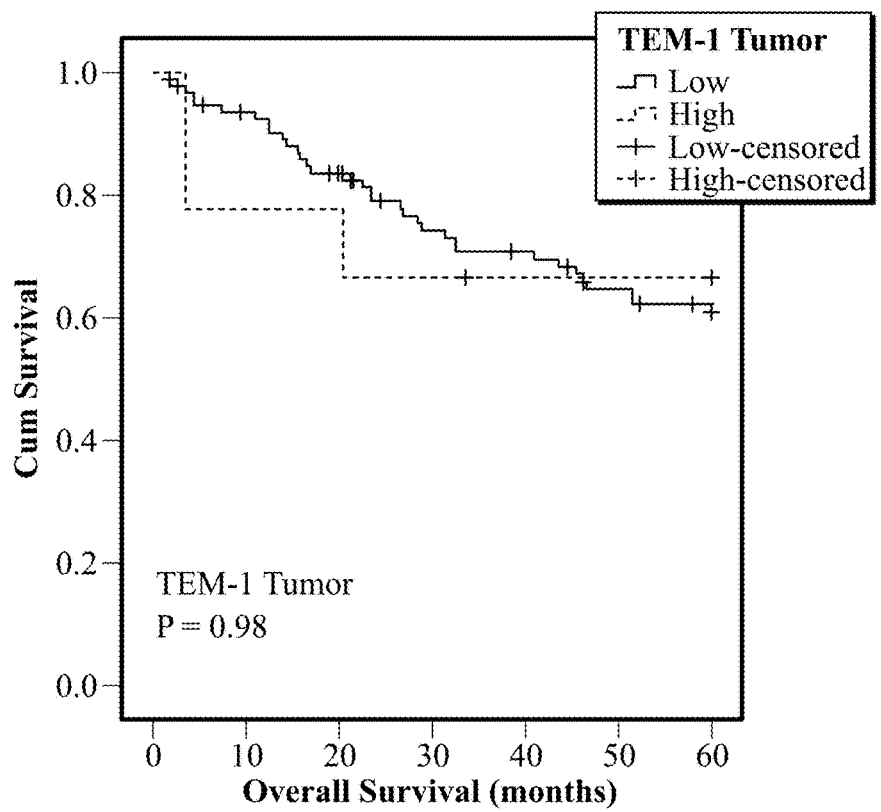
FIG. 5(A-D) shows Kaplan-Meier survival analysis of the validation set for endosialin/TEM-1 expression in all compartments.
Figure 5B:
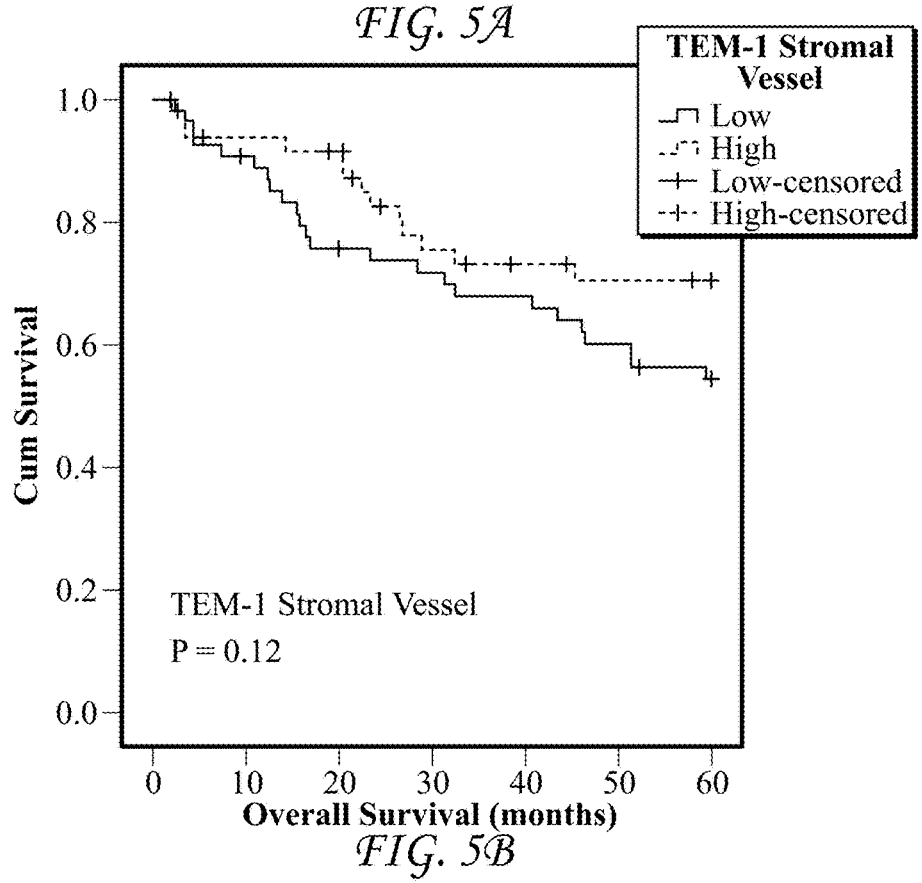
Figure 5C:
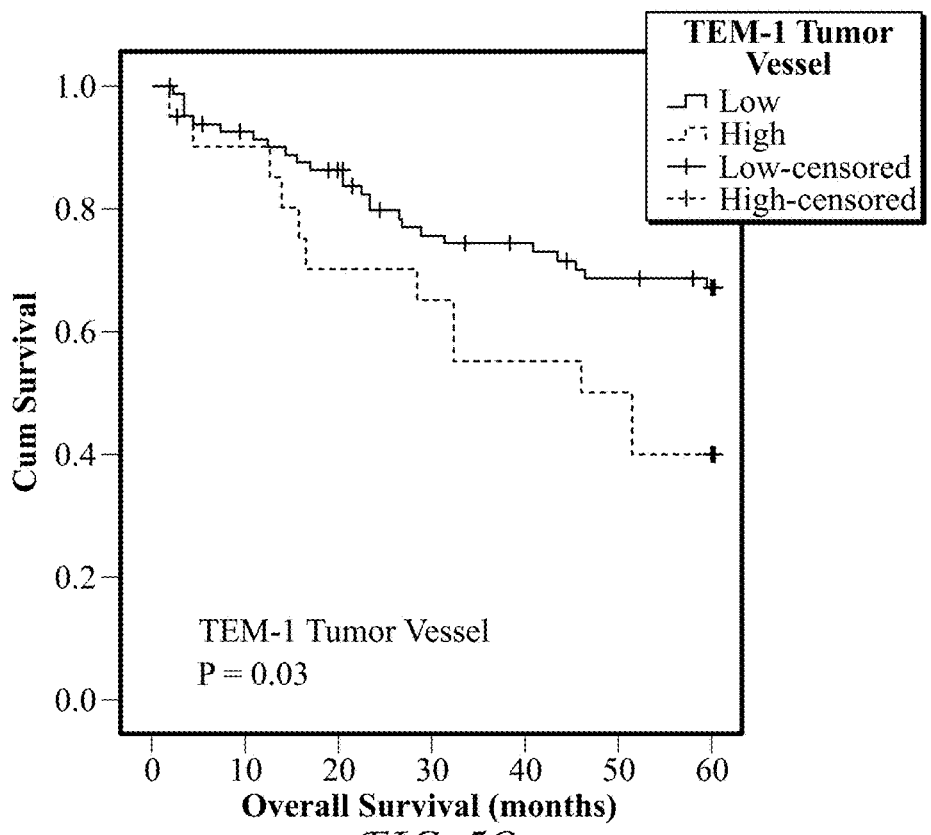
Figure 5D:
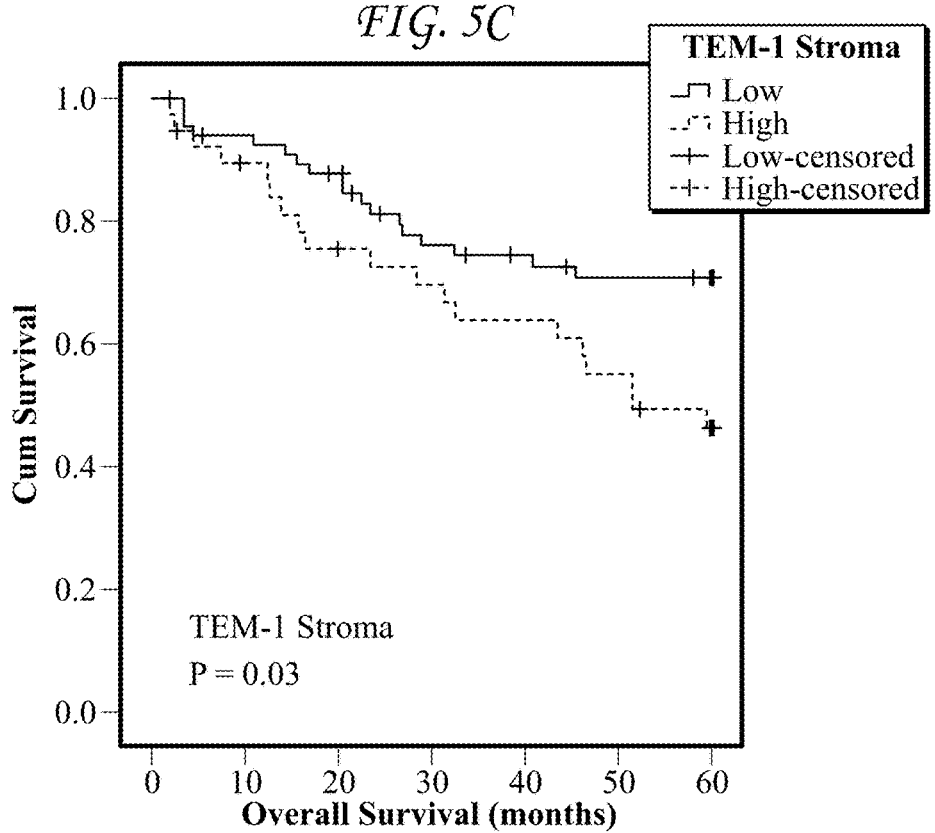

Since all TEM-1 associated biomarkers (TEM-1, HIF2α, CAIX, PDGFR-β, fibronectin (FN), collagen I, and collagen IV) have shown putative expression in both tumor and stromal cellular compartments, experiments were conducted to examine total tissue level expression on the CRC cohort (Table 6). Unsupervised hierarchical clustering revealed two main patient clusters (FIG. 3). In "gene" cluster 1, all patients express relatively low levels of all proteins, while in cluster 2, all patient samples express relatively high levels of all proteins except CAIX. For biomarker ("array") clustering, endosialin/TEM-1 clustered most closely with PDGFR-β, Collagen I, and Collagen IV. This also bore out in bivariate correlation analysis with significant (p<0.001) Spearman's Rho correlation coefficients of 0.62, 0.43, and 0.31, respectively. A complete bivariate correlation analysis is provided in Table 7. CAIX did not cluster with any of the other biomarkers tested and thus is the least related. Survival outcomes were examined as a function of total expression, although all markers demonstrated an optimal cut-point on the training set that significantly (p<0.10) predicted survival, none of these cut-points validated in the validation set.

TABLE 6

| | Training Set (n = 330) | | | Validation Set (N = 164) | | | |
|---|---|---|---|---|---|---|---|
| Variable | N*(%) | HR^ (95% CI) | P^ | N(%) | HR (95% CI) | P | χ²P |
| Duke's Stage | | | | | | | |
| I | 74 (23) | | | 31 (21) | | | |
| II | 84 (27) | 2.7 (1.3-5.5) | 0.008 | 42 (28) | 1.8 (0.7-4.6) | 0.24 | 0.37 |
| III | 130 (41) | 3.8 (3.0-11.2) | <0.001 | 55 (37) | 3.3 (1.4-8.1) | 0.007 | |
| IV | 29 (9) | 3.0 (1.2-7.2) | 0.02 | 21 (14) | 1.3 (0.4-4.1) | 0.71 | |
| Grade | | | | | | | |
| Well | 103 (38) | | | 60 (46) | | | 0.20 |
| Moderate | 140 (52) | 1.2 (0.8-1.8) | 0.40 | 55 (42) | 1.6 (0.8-2.9) | 0.15 | |
| Poor | 27 (10) | 1.1 (0.6-2.3) | 0.70 | 15 (12) | 2.1 (0.3-5.0) | 0.10 | |
| Sex | | | | | | | |
| Female | 176 (53) | | | 98 (60) | | | 0.18 |
| Male | 154 (47) | 1.4 (1.0-2.0) | 0.05 | 66 (40) | 1.4 (0.8-2.9) | 0.2 | |
| Age | | | | | | | |
| 40-50 | 16 (5) | | | 9 (6) | | | 0.89 |
| 50-60 | 68 (21) | 0.6 (0.3-1.4) | 0.29 | 95 (21) | 0.5 (0.2-1.2) | 0.12 | |
| 60-70 | 107 (32) | 0.6 (0.3-1.4) | 0.28 | 49 (30) | 0.4 (0.2-1.1) | 0.09 | |
| >70 | 133 (42) | 0.8 (0.3-1.7) | 0.49 | 71 (43) | 0.5 (0.2-1.5) | 0.30 | |

*Clinical data not available on all cases; percentage based on total number in category ^Hazard ratios(HR), 95% Confidence Intervals (95% CI), and P-values (P) based on 5-year disease specific Cox proportional hazards modeling.

TABLE 7

| | | TEM-1 | PDGFR | Fibronectin | CAIX | HIF2α | Collagen I | Collagen IV |
|---|---|---|---|---|---|---|---|---|
| TEM-1 | Correlation Coefficient | | .624** | .293** | .168** | .284** | .431** | .310** |
| | Sig. (2-tailed) | | .000 | .000 | .004 | .000 | .000 | .000 |
| PDGFR | Correlation Coefficient | .624** | | .333** | .240** | .449** | .652** | .497** |
| | Sig. (2-tailed) | .000 | | .000 | .000 | .000 | .000 | .000 |
| Fibronectin | Correlation Coefficient | .293** | .333** | | .058 | .543** | .469** | .449** |
| | Sig. (2-tailed) | .000 | .000 | | .331 | .000 | .000 | .000 |
| CAIX | Correlation Coefficient | .168** | .240** | .058 | | .119* | .127* | .061 |
| | Sig. (2-tailed) | .004 | .000 | .331 | | .042 | .027 | .300 |
| HIF2α | Correlation Coefficient | .284** | .449** | .543** | .119* | | .465** | .302** |
| | Sig. (2-tailed) | .000 | .000 | .000 | .042 | | .000 | .000 |
| Collagen I | Correlation Coefficient | .431** | .652** | .469** | .127* | .465** | | .644** |
| | Sig. (2-tailed) | .000 | .000 | .000 | .027 | .000 | | .000 |
| Collagen IV | Correlation Coefficient | .310** | .497** | .449** | .061 | .302** | .644** | |
| | Sig. (2-tailed) | .000 | .000 | .000 | .300 | .000 | .000 | |

Example 6: Cellular Compartment-Specific Expression of Biomarkers

Since it is known that the biomarkers of interest can have varied cellular expression, compartment specific "masks" were developed to specifically identify and isolate tumor, stroma, stromal-specific vasculature, and tumor-specific vasculature. In brief, each endosialin/TEM-1 associated biomarker was combined with DAPI to identify nuclei, cytokeratin to identify tumor cytoplasm, vimentin to identify stroma and CD-31 to identify vasculature. Advanced image analysis algorithms were then used to generate a binary image identifying each pixel as either included or excluded from each compartment of interest. AQUA scores for each biomarker were generated for 4 biological compartments of interest: tumor (membrane/cytoplasm), tumor vessel, stroma (stroma without contributing vasculature), and stromal vessel. Means analysis showed significant differential expression by compartment (FIG. 4A-G). All markers, except for CAIX, showed significantly higher level expression in stroma and/or vasculature compared to tumor. Conversely, CAIX showed higher level expression in tumor and tumor vessel compared to stromal components. Expression as a function of available clinical variables showed only minimal association (data not shown). Namely, PDGFR-D and Collagen IV showed significantly increased expression in males compared to females; and stromal fibronectin and Collagen I showed increase expression as a function of advanced stage of disease.

Example 7: Univariate Survival Analysis

Optimal Kaplan-Meier survival cutpoints were defined within continuous AQUA score data using X-Tile for optimal cut-point analysis on the training set (Table 6) and subsequently applied to the validation set. A biomarker was considered to validate if significance (p<0.05) was reached in both the training set and validation set. Five-year disease-free survival data for each individual marker/compartment combination is summarized in Table 8. Although all markers showed a trend for association with survival (Training p<0.20), tumor vessel and stromal TEM-1 expression, as well as stromal vessel Collagen I and HIF2α, were the only biomarkers to validate in the univariate setting. High tumor vessel and stromal TEM-1 expression as well as stromal vessel HIF2α, associated with increased five-year disease specific survival (HR=0.47/p=0.03; HR=0.49/p=0.03; and HR=0.33/p=0.02 respectively), while high stromal vessel Collagen I expression associated with decrease five-year survival (HR=2.31/p=0.008). Kaplan-Meier survival analysis of the validation set for endosialin/TEM-1 expression in all compartments is shown in FIG. 5A-D demonstrating the differential survival benefit and thus justification for quantifying biomarker expression in distinct cellular compartments.

Example 8: Generation of R-TAPPS Score

Because of the association of the markers described herein (FIG. 5) and the putative impact they may collectively have on both survival as well as potential response to endosialin/TEM-1 targeted therapy via ontuxizumab, we combined markers together in a multivariate Cox Proportional Hazards model using the univariate cut-points. Criteria for initial entry into the model was significance at the 20% level in both the training set and validation set (biomarkers highlighted in bold in Table 8; n=13). Using backward elimination modeling based on Wald statistics on the training set, the starting model of 13 biomarkers, was refined down to 5 biomarkers (Table 9): TEM-1 stroma, TEM-1 tumor vessel, HIF2α stromal vessel, Collagen IV tumor, and FN stroma. This overall model was highly significant with p-value of $9.0 \times 10^{-8}$.

TABLE 8

| Marker | Optimal Cut (% High) | Training P | Validation HR (95% CI) | Validation P |
|---|---|---|---|---|
| TEM-1 Tumor | 618.30 (10.1) | 0.10 | 0.99 (0.30-3.21) | 0.98 |
| TEM-1 Stromal Vessel | 635.84 (50.7) | 0.12 | 0.59 (0.30-1.16) | 0.12 |
| TEM-1 Tumor Vessel | 364.27 (85.0) | 0.19 | 0.47 (0.24-0.94) | 0.03 |

TABLE 8-continued

| Marker | Optimal Cut (% High) | Training P | Validation HR (95% CI) | Validation P |
| --- | --- | --- | --- | --- |
| TEM-1 Stroma | 473.58 (65.2) | 0.012 | 0.49 (0.26-0.94) | 0.03 |
| PDGFR-β Tumor | 1407.43 (13.1) | 0.007 | 0.37 (0.10-1.56) | 0.16 |
| PDGFR-β Stromal Vessel | 3803.74 (25.2) | 0.12 | 1.86 (0.92-3.76) | 0.08 |
| PDGFR-β Tumor Vessel | 1060.14 (20.9) | 0.005 | 0.93 (0.41-2.12) | 0.86 |
| PDGFR-β Stroma | 6438.14 (15.1) | 0.007 | 0.87 (0.33-2.60) | 0.87 |
| Collagen I Tumor | 853.82 (49.6) | 0.0001 | 1.61 (0.86-3.02) | 0.13 |
| Collagen I Stromal Vessel | 2587.16 (25.2) | <0.0001 | 2.31 (1.22-4.35) | 0.008 |
| Collagen I Tumor Vessel | 1653.24 (24.0) | 0.0004 | 1.33 (0.65-2.72) | 0.43 |
| Collagen I Stroma | 3285.71 (28.8) | 0.001 | 1.36 (0.72-2.56) | 0.34 |
| Collagen IV Tumor | 467.87 (45.7) | 0.0001 | 1.59 (0.84-3.01) | 0.15 |
| Collagen IV Stroma Vessel | 1832.17 (31.7) | 0.0052 | 1.28 (0.62-2.63) | 0.51 |
| Collagen IV Tumor Vessel | 608.21 (48.9) | 0.0038 | 1.31 (0.69-2.48) | 0.41 |
| Collagen IV Stroma | 2602.54 (14.0) | 0.0023 | 1.26 (0.49-3.22) | 0.63 |
| FN Tumor | 5156.43 (52.3) | 0.0017 | 1.50 (0.77-2.92) | 0.23 |
| FN Stroma Vessel | 5239.83 (55.8) | 0.021 | 1.28 (0.65-2.53) | 0.47 |
| FN Tumor Vessel | 6119.94 (33.5) | 0.004 | 1.82 (0.89-3.72) | 0.10 |
| FN Stroma | 10380.35 (12.2) | 0.0001 | 2.03 (0.72-5.75) | 0.17 |
| HIF2α Tumor | 1738.02 (31.8) | 0.048 | 0.76 (0.35-1.66) | 0.49 |
| HIF2α Stromal Vessel | 1881.86 (26.1) | 0.008 | 0.33 (0.13-0.86) | 0.02 |
| HIF2α Tumor Vessel | 1054.97 (65.4) | 0.200 | 0.61 (0.33-1.14) | 0.12 |
| HIF2α Stroma | 2005.59 (61.6) | 0.083 | 0.86 (0.45-1.64) | 0.65 |
| CAIX Tumor | 598.58 (88.4) | 0.02 | 1.20 (0.37-3.90) | 0.76 |
| CAIX Stroma Vessel | 2214.02 (13.4) | 0.01 | 0.89 (0.23-3.12) | 0.62 |
| CAIX Tumor Vessel | 2641.25 (21.8) | 0.002 | 0.52 (0.23-1.19) | 0.16 |
| CAIX Stroma | 2637.22 (15.7) | 0.04 | 0.84 (0.37-1.91) | 0.69 |

Taking the model coefficients for each marker (Table 9) an equation termed "the refined TAPPS" (TEM-1 Associated Pathway Prognostic Signature) score was developed that would provide an overall risk score. The R-TAPPS score is defined as:

$$\text{R-TAPPS} = (\text{TEM-1Stroma}_{(0/1)} * -0.89) + (\text{TEM-1Tumor Vessel}_{(0/1)} * 1.19) + (\text{HIF2}\alpha \text{ Stromal Vessel}_{(0/1)} * -0.76) + (\text{Collagen IV Tumor}_{(0/1)} * 0.62) + (FN \text{ Stroma}_{(0/1)} * 0.83).$$

TABLE 9

| Model | Marker | HR | 95% CI | P-value | Coefficient | Model P |
| --- | --- | --- | --- | --- | --- | --- |
| Full | TEM1 Stroma | 0.41 | 0.24-0.69 | 0.001 | −0.89 | $9.0 \times 10^{-8}$ |
| | TEM1 Tumor Vessel | 3.27 | 1.35-7.95 | 0.009 | 1.19 | |
| | HIF2α Stromal Vessel | 0.47 | 0.25-0.88 | 0.02 | −0.76 | |
| | Collagen IV Tumor | 1.86 | 1.08-3.21 | 0.03 | 0.62 | |
| | FN Stroma | 2.29 | 1.23-3.21 | 0.009 | 0.83 | |
| | TAPPS (Training) | 1.76 | 1.44-2.15 | <0.001 | NA | $4.3 \times 10^{-9}$ |
| | TAPPS (Validation) | 1.38 | 1.02-1.88 | 0.041 | NA | 0.04 |
| Minimal | TEM-1 Stroma | 0.58 | 0.36-0.93 | 0.03 | −0.55 | 0.000009 |
| | Collagen IV Tumor | 1.90 | 1.12-3.25 | 0.02 | 0.64 | |
| | FN Stroma | 2.18 | 1.18-4.05 | 0.01 | 0.78 | |
| | mTAPPS (Training) | 2.72 | 1.82-4.08 | <0.001 | NA | $5.3 \times 10^{-7}$ |
| | mTAPPS (Validation) | 2.66 | 1.26-5.62 | 0.01 | NA | 0.045 |

The resultant R-TAPPS score had a range of −0.89 to 3.88 with a median score of 1.13. As a continuous variable on the training set, as expected the R-TAPPS score significantly associated with decreased survival [HR=1.76 (95% CI: 1.44-2.15); p=$4.3 \times 10^{-9}$; Table 3], but then was applied to the validation set with significance [HR=1.38 (95% CI: 1.02-1.88); p=0.04; Table 3]. The R-TAPPS score was independent and provided significant added prognostic value [HR=1.66 (95% CI: 1.37-2.03); p<0.001; LR-$\chi^2$=67.2] when put into the highly significant model with known clinical variables (LR-$\chi^2$=49.7).

Figure 6A:
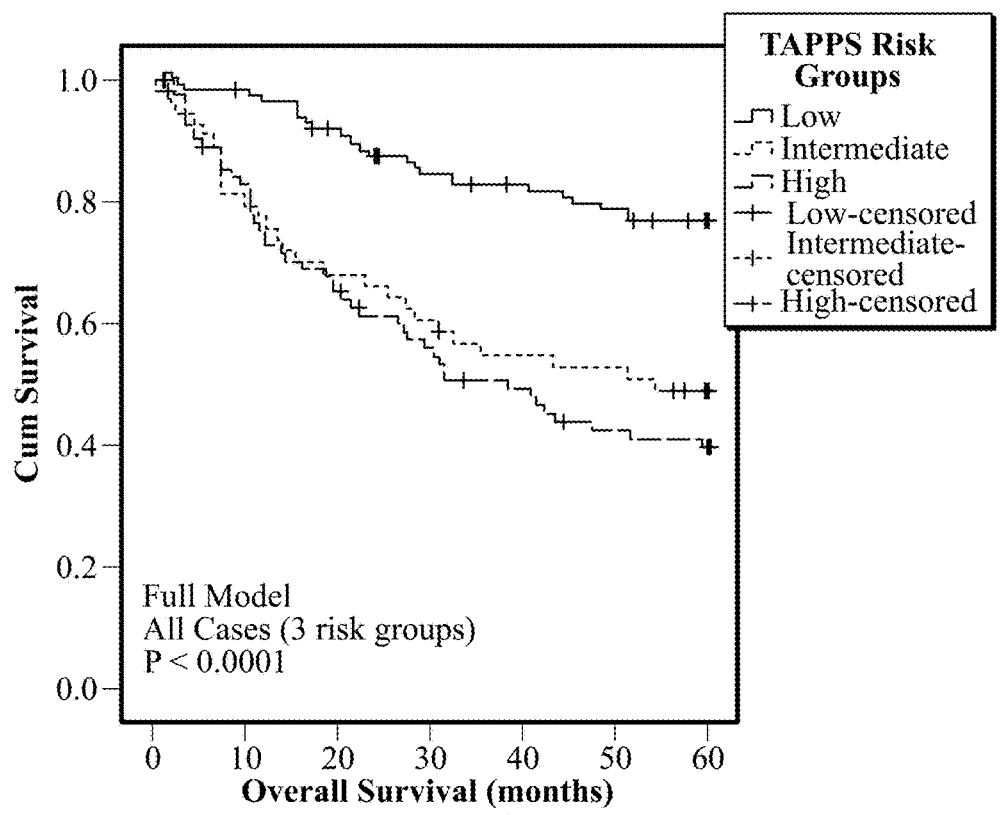
FIG. 6 shows Kaplan-Meier survival analysis for (A) low-, intermediate-, and high-censored risk groups; (B) low- and high-censored risk groups, (C) stage II colorectal cancer patients, and (D) stage III/IV colorectal cancer patients.
Figure 6B:
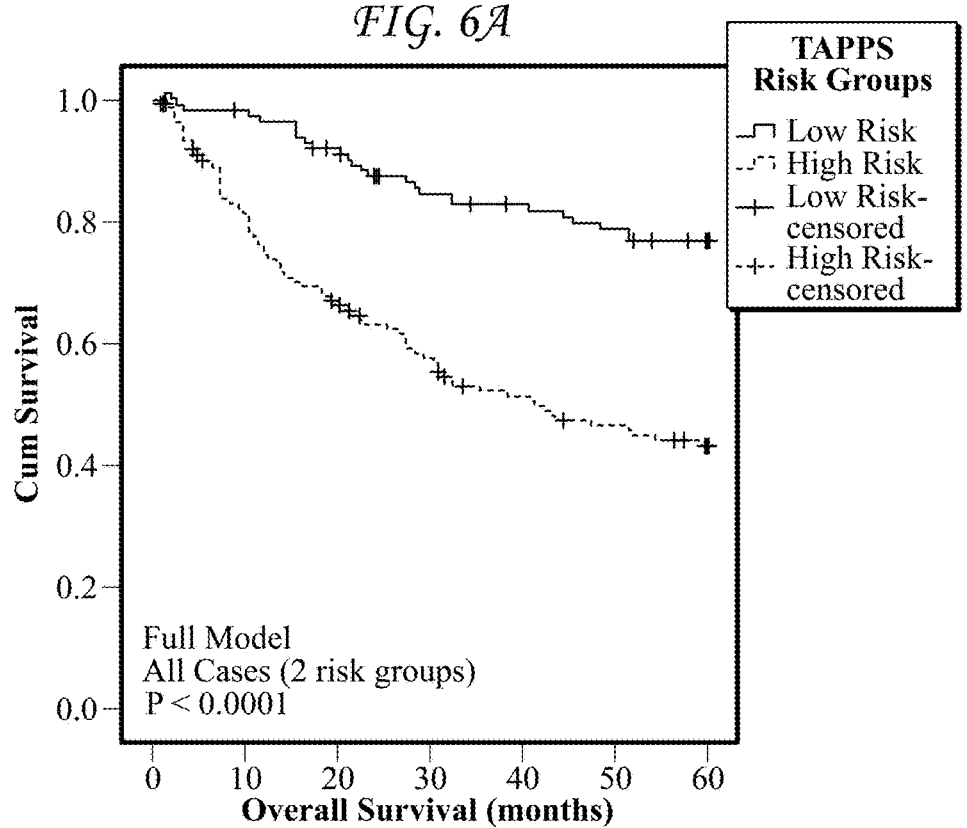

In order for the R-TAPPS score to be used as a diagnostic in a clinical setting, risk groups (i.e. Oncotype Dx) should be established as a function of the continuous risk score to allow for classification of patients. Therefore, the R-TAPPS score was divided into tertiles representing 3 groups, putatively low risk (R-TAPPS<0.3), intermediate risk (R-TAPPS 0.3-1.86), and high risk (R-TAPPS>1.86). However, when survival was examined by Kaplan-Meier, although highly significant (P<0.0001), there was no substantial difference between intermediate and high risk groups (FIG. 6A). Thus, the intermediate and high risk groups were combined to form one high risk group (FIG. 6B).

Figure 6C:
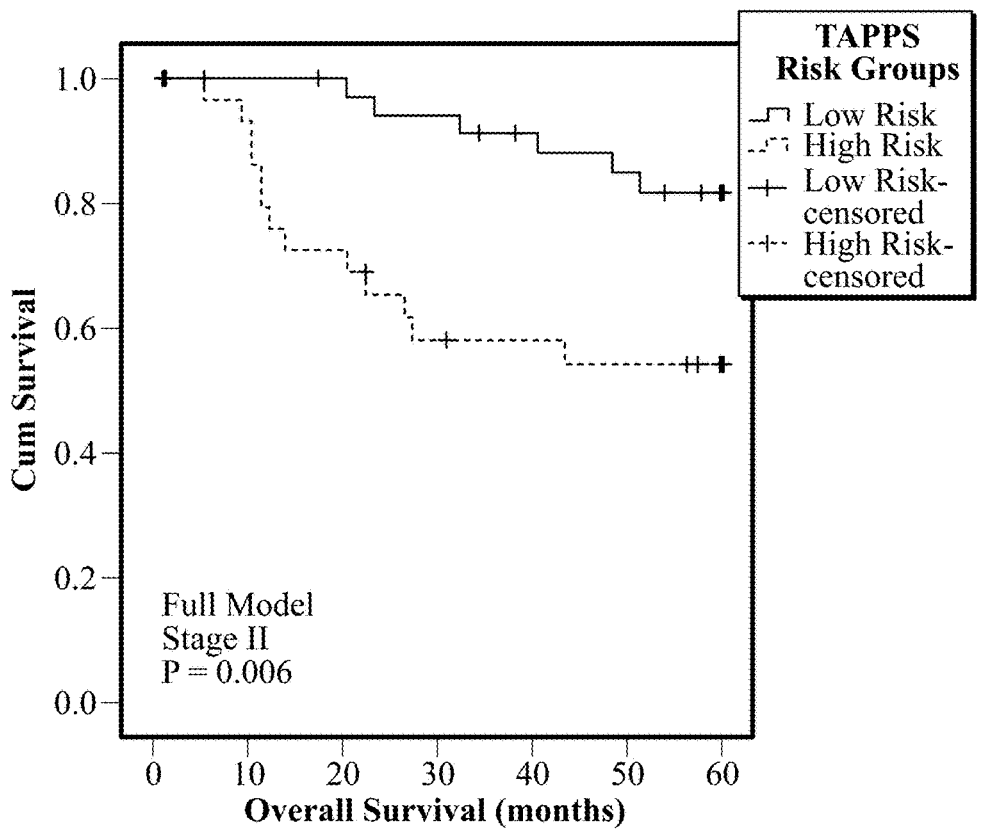
Figure 6D:
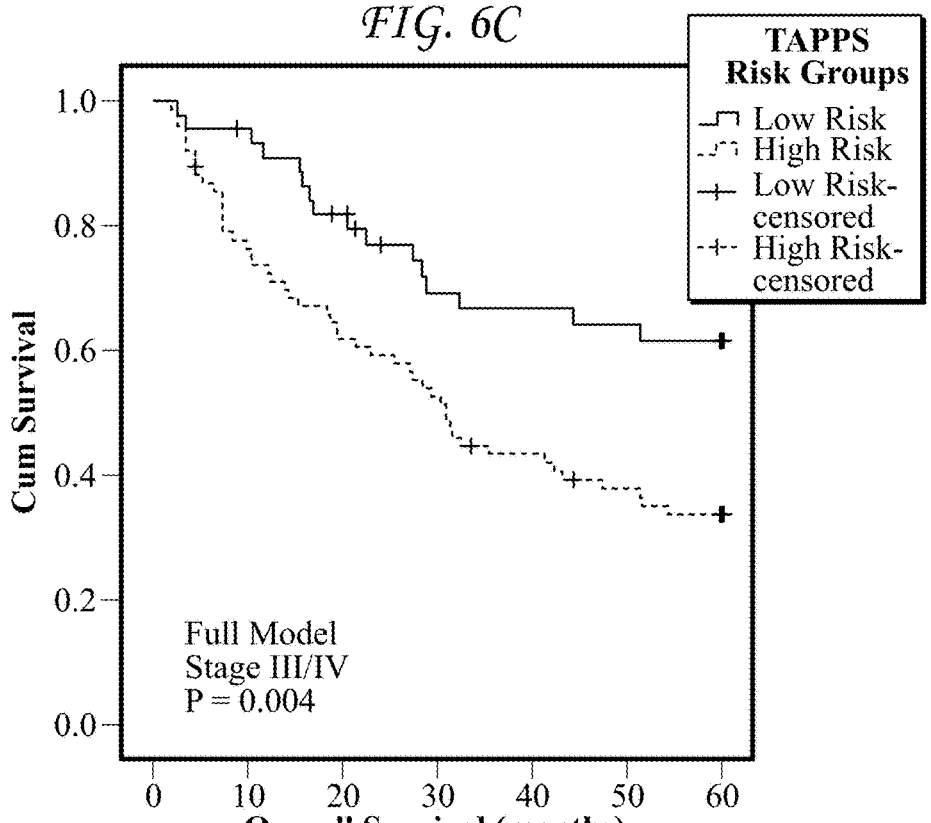

An important clinical question in the treatment of CRC is whether to provide chemotherapy for Stage II patients; therefore, analyses were conducted to examiner the association of R-TAPPS risk groups in Stage II patients. The resulting observations showed a highly significant association (p=0.006) with survival (FIG. 6C). We also observed a significant association in Stage III/IV patients (FIG. 6D).

Figure 7A:
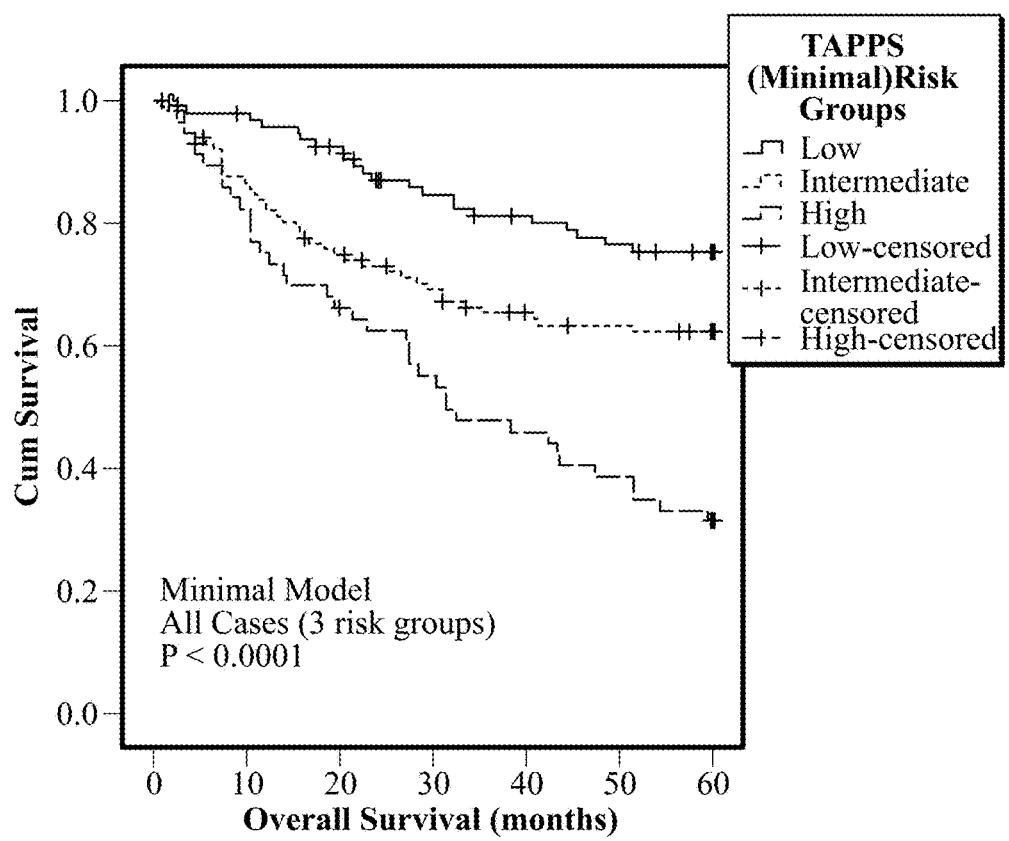
FIG. 7 shows Kaplan-Meier survival analysis for a model including only 3 variable parameters for (A) all cases and (B) stage II colorectal cancer patients.
Figure 7B:
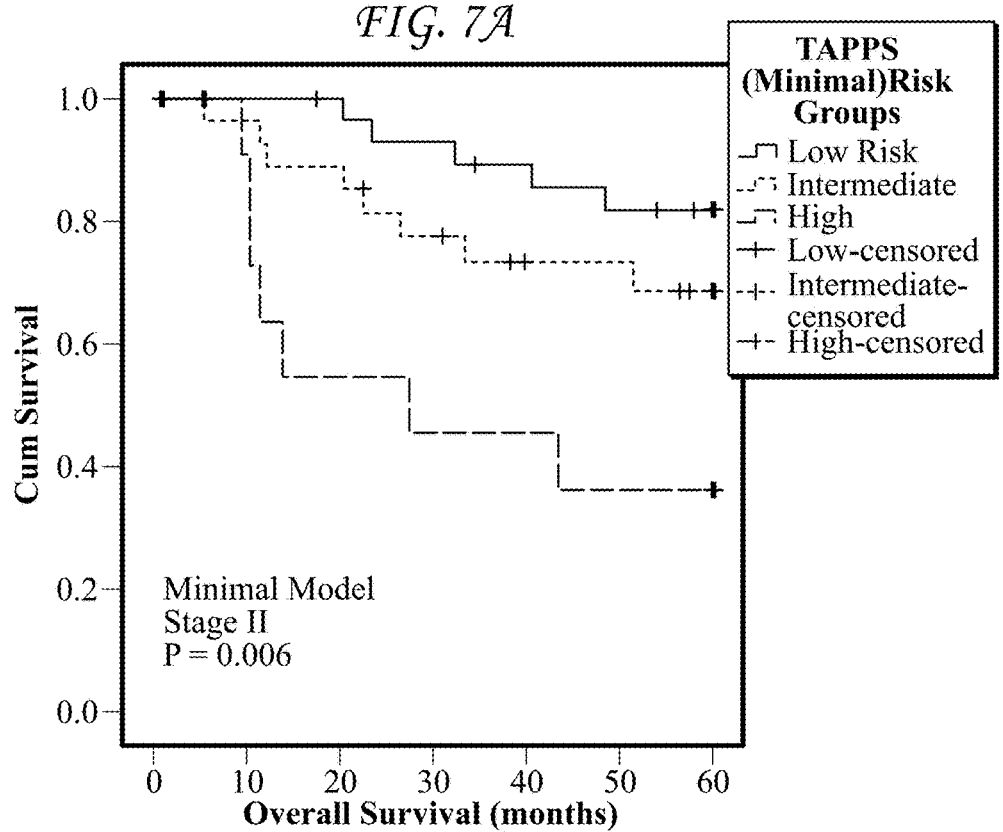

For validation of the assay and to assess whether fewer markers could yield useful results studies were conducted to reduce the number of markers in the model. Removing the vessel markers would eliminate a moving part in the assay, namely the requirement for the CD31 (vasculature) compartment. Therefore, a model with only TEM-1 Stroma, Collagen IV Tumor and FN Stroma was tested (FIG. 7). Although this minimal model did not provide as much prognostic value (LR-$\chi^2$=32.2 for the minimal versus LR-$\chi^2$=37.2 for the full model), it was nonetheless highly significant [HR=2.7 (95% CI: 1.9-3.8); p=$2.5 \times 10^{-8}$).

What is claimed:

1. A tissue sample array comprising colorectal cancer tissue samples, wherein the array is labeled with antibodies consisting of an antibody that specifically binds cytokeratin, an antibody that specifically binds vimentin, an antibody that specifically binds TEM1, an antibody that specifically binds fibronectin-1, and an antibody that specifically binds collagen IV.

2. The tissue sample array of claim 1, wherein one or more of the colorectal cancer tissue samples is labeled with a nuclear label.

3. The tissue sample array of claim 2, wherein the nuclear label is DAPI.

4. The tissue sample array of claim 2, wherein the colorectal cancer tissue samples of the array are obtained from the same tumor.

5. The tissue sample array of claim 4, wherein the colorectal cancer tissue samples are histological sections.

6. The tissue sample array of claim 2, wherein the colorectal cancer tissue samples of the array are obtained from different tumors.

7. The tissue sample array of claim 6, wherein the colorectal cancer tissue samples are histological sections.

8. The tissue sample array of claim 1, wherein the colorectal cancer tumor tissue samples of the array are obtained from the same tumor.

9. The tissue sample array of claim 1, wherein the colorectal cancer tissue samples of the array are obtained from different tumors.

10. The tissue sample array of claim 8, wherein the colorectal cancer tissue samples are histological sections.

11. The tissue sample array of claim 9, wherein the colorectal cancer tissue samples are histological sections.

12. A tissue sample array comprising colorectal cancer tissue samples, wherein the array is labeled with antibodies consisting of an antibody that specifically binds cytokeratin, an antibody that specifically binds vimentin, an antibody that specifically binds TEM1, an antibody that specifically binds fibronectin-1, an antibody that specifically binds collagen IV, an antibody that specifically binds CD31, and an antibody that specifically binds HIF2α.

13. The tissue sample array of claim 12, wherein the array comprises:
a plurality of colorectal cancer tissue samples labeled with an antibody that specifically binds vimentin,
a plurality of colorectal cancer tissue samples labeled with an antibody that specifically binds cytokeratin and a second antibody that specifically binds CD31,
a plurality of colorectal cancer tissue samples labeled with an antibody that specifically binds vimentin and a second antibody that specifically binds CD31,
a plurality of colorectal cancer tissue samples labeled with an antibody that specifically binds cytokeratin,
wherein,
at least one colorectal cancer tissue sample labeled with an antibody that specifically binds vimentin is also labeled with an antibody that specifically binds TEM-1,
at least one colorectal cancer tissue sample labeled with an antibody that specifically binds cytokeratin and a second antibody that specifically binds CD31 is also labeled with an antibody that specifically binds TEM-1,
at least one colorectal cancer tissue sample labeled with an antibody that specifically binds vimentin and a second antibody that specifically binds CD31 is also labeled with an antibody that specifically binds HIF2α,
at least one colorectal cancer tissue sample labeled with an antibody that specifically binds cytokeratin is also labeled with an antibody that specifically binds collagen IV, and
at least one colorectal cancer tissue sample labeled with an antibody that specifically binds vimentin is also labeled with an antibody that specifically binds fibronectin-1.

14. The tissue sample array of claim 12, wherein the array comprises:
a plurality of colorectal cancer tissue samples labeled with an antibody that specifically binds vimentin, and
a plurality of colorectal cancer tissue samples labeled with an antibody that specifically binds cytokeratin,
wherein,
at least one colorectal cancer tissue sample labeled with an antibody that specifically binds vimentin is also labeled with an antibody that specifically binds TEM-1,
at least one colorectal cancer tissue sample labeled with an antibody that specifically binds cytokeratin is also labeled with an antibody that specifically binds collagen IV, and
at least one colorectal cancer tissue sample labeled with an antibody that specifically binds vimentin is also labeled with an antibody that specifically binds fibronectin-1.

* * * * *